United States Patent
Dobie et al.

(10) Patent No.: US 8,198,253 B2
(45) Date of Patent: Jun. 12, 2012

(54) COMPOSITIONS AND THEIR USES DIRECTED TO HBXIP

(75) Inventors: Kenneth W. Dobie, Del Mar, CA (US); Nicholas M. Dean, Olivenhain, CA (US); C. Frank Bennett, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/374,635

(22) PCT Filed: Jul. 18, 2007

(86) PCT No.: PCT/US2007/073799
§ 371 (c)(1),
(2), (4) Date: Oct. 13, 2009

(87) PCT Pub. No.: WO2008/011473
PCT Pub. Date: Jan. 24, 2008

(65) Prior Publication Data
US 2010/0056607 A1 Mar. 4, 2010

Related U.S. Application Data

(60) Provisional application No. 60/807,803, filed on Jul. 19, 2006.

(51) Int. Cl.
C07H 21/02 (2006.01)
C07H 21/04 (2006.01)
A61K 31/70 (2006.01)
C12Q 1/68 (2006.01)

(52) U.S. Cl. ...... 514/44 A; 435/375; 435/377; 536/23.1; 536/24.1; 536/24.5

(58) Field of Classification Search ............ None
See application file for complete search history.

(56) References Cited

U.S. PATENT DOCUMENTS

| | | | |
|---|---|---|---|
| 3,687,808 A | 8/1972 | Merigan et al. |
| 4,426,330 A | 1/1984 | Sears |
| 4,469,863 A | 9/1984 | Ts'o |
| 4,476,301 A | 10/1984 | Imbach et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,556 A | 5/1991 | Woodle et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,213,804 A | 5/1993 | Martin et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,223,618 A | 6/1993 | Cook et al. |
| 5,227,170 A | 7/1993 | Sullivan |
| 5,235,033 A | 8/1993 | Summerton et al. |
| 5,245,022 A | 9/1993 | Weis et al. |

(Continued)

FOREIGN PATENT DOCUMENTS

| | | |
|---|---|---|
| WO | WO 93/07883 | 4/1993 |
| WO | WO 93/24510 | 12/1993 |
| WO | WO 94/02499 | 2/1994 |
| WO | WO 94/17093 | 8/1994 |
| WO | WO 94/26764 | 11/1994 |
| WO | WO 97/26270 | 7/1997 |
| WO | WO 98/39352 | 11/1998 |
| WO | WO 99/14226 | 3/1999 |
| WO | WO 03/004602 | 1/2003 |

OTHER PUBLICATIONS

GenBank Accession No. NM_006402.2 published by NCBI on Dec. 5, 2003 [retrieved on Feb. 13, 2010].*

(Continued)

Primary Examiner — Sean McGarry

(74) Attorney, Agent, or Firm — Jones Day

(57) ABSTRACT

Disclosed herein are compounds, compositions and methods for modulating the expression of HBXIP in a cell, tissue or animal. Also provided are methods of target validation. Also provided are uses of disclosed compounds and compositions in the manufacture of a medicament for treatment of diseases and disorders.

18 Claims, No Drawings

U.S. PATENT DOCUMENTS

| | | | |
|---|---|---|---|
| 5,254,469 A | 10/1993 | Warren, III et al. | |
| 5,256,775 A | 10/1993 | Froehler | |
| 5,258,506 A | 11/1993 | Urdea et al. | |
| 5,262,536 A | 11/1993 | Hobbs, Jr. | |
| 5,264,221 A | 11/1993 | Tagawa et al. | |
| 5,264,423 A | 11/1993 | Cohen et al. | |
| 5,264,562 A | 11/1993 | Matteucci | |
| 5,264,564 A | 11/1993 | Matteucci | |
| 5,272,250 A | 12/1993 | Spielvogel et al. | |
| 5,276,019 A | 1/1994 | Cohen et al. | |
| 5,278,302 A | 1/1994 | Caruthers et al. | |
| 5,286,717 A | 2/1994 | Cohen et al. | |
| 5,292,873 A | 3/1994 | Rokita et al. | |
| 5,317,098 A | 5/1994 | Shizuya et al. | |
| 5,319,080 A | 6/1994 | Leumann | |
| 5,321,131 A | 6/1994 | Agrawal et al. | |
| 5,354,844 A | 10/1994 | Beug et al. | |
| 5,356,633 A | 10/1994 | Woodle et al. | |
| 5,359,044 A | 10/1994 | Cook et al. | |
| 5,366,878 A | 11/1994 | Pederson et al. | |
| 5,367,066 A | 11/1994 | Urdea et al. | |
| 5,371,241 A | 12/1994 | Brush | |
| 5,378,825 A | 1/1995 | Cook et al. | |
| 5,386,023 A | 1/1995 | Sanghvi et al. | |
| 5,391,723 A | 2/1995 | Priest | |
| 5,393,878 A | 2/1995 | Leumann | |
| 5,395,619 A | 3/1995 | Zalipsky et al. | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,414,077 A | 5/1995 | Lin et al. | |
| 5,416,016 A | 5/1995 | Low et al. | |
| 5,416,203 A | 5/1995 | Letsinger | |
| 5,417,978 A | 5/1995 | Tari et al. | |
| 5,432,272 A | 7/1995 | Benner | |
| 5,434,257 A | 7/1995 | Matteucci et al. | |
| 5,446,137 A | 8/1995 | Maag et al. | |
| 5,451,463 A | 9/1995 | Nelson et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,127 A | 10/1995 | Felgner et al. | |
| 5,459,255 A | 10/1995 | Cook et al. | |
| 5,462,854 A | 10/1995 | Coassin et al. | |
| 5,466,677 A | 11/1995 | Baxter et al. | |
| 5,466,786 A | 11/1995 | Buhr et al. | |
| 5,469,854 A | 11/1995 | Unger et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,486,603 A | 1/1996 | Buhr | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,506,351 A | 4/1996 | McGee | |
| 5,508,270 A | 4/1996 | Baxter et al. | |
| 5,510,475 A | 4/1996 | Agrawal et al. | |
| 5,512,295 A | 4/1996 | Kornberg et al. | |
| 5,512,439 A | 4/1996 | Hornes et al. | |
| 5,512,667 A | 4/1996 | Reed et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,521,291 A | 5/1996 | Curiel et al. | |
| 5,525,465 A | 6/1996 | Haralambidis et al. | |
| 5,525,711 A | 6/1996 | Hawkins et al. | |
| 5,527,528 A | 6/1996 | Allen et al. | |
| 5,527,899 A | 6/1996 | Froehler | |
| 5,534,259 A | 7/1996 | Zalipsky et al. | |
| 5,536,821 A | 7/1996 | Agrawal et al. | |
| 5,539,082 A | 7/1996 | Nielsen et al. | |
| 5,541,306 A | 7/1996 | Agrawal et al. | |
| 5,541,307 A | 7/1996 | Cook et al. | |
| 5,541,313 A | 7/1996 | Ruth | |
| 5,543,152 A | 8/1996 | Webb et al. | |
| 5,543,158 A | 8/1996 | Gref et al. | |
| 5,545,730 A | 8/1996 | Urdea et al. | |
| 5,547,932 A | 8/1996 | Curiel et al. | |
| 5,550,111 A | 8/1996 | Suhadolnik et al. | |
| 5,552,538 A | 9/1996 | Urdea et al. | |
| 5,552,540 A | 9/1996 | Haralambidis et al. | |
| 5,556,948 A | 9/1996 | Tagawa et al. | |
| 5,561,225 A | 10/1996 | Maddry et al. | |
| 5,563,253 A | 10/1996 | Agrawal et al. | |
| 5,565,350 A | 10/1996 | Kmiec | |
| 5,565,552 A | 10/1996 | Magda et al. | |
| 5,565,555 A | 10/1996 | Froehler et al. | |
| 5,567,810 A | 10/1996 | Weis et al. | |
| 5,567,811 A | 10/1996 | Misiura et al. | |
| 5,571,799 A | 11/1996 | Tkachuk et al. | |
| 5,574,142 A | 11/1996 | Meyer, Jr. et al. | |
| 5,576,427 A | 11/1996 | Cook et al. | |
| 5,578,717 A | 11/1996 | Urdea et al. | |
| 5,578,718 A | 11/1996 | Cook et al. | |
| 5,580,575 A | 12/1996 | Unger et al. | |
| 5,580,731 A | 12/1996 | Chang et al. | |
| 5,583,020 A | 12/1996 | Sullivan | |
| 5,585,481 A | 12/1996 | Arnold, Jr. et al. | |
| 5,587,361 A | 12/1996 | Cook et al. | |
| 5,587,371 A | 12/1996 | Sessler et al. | |
| 5,587,469 A | 12/1996 | Cook et al. | |
| 5,591,584 A | 1/1997 | Chang et al. | |
| 5,591,721 A | 1/1997 | Agrawal et al. | |
| 5,591,722 A | 1/1997 | Montgomery et al. | |
| 5,594,121 A | 1/1997 | Froehler et al. | |
| 5,595,726 A | 1/1997 | Magda et al. | |
| 5,595,756 A | 1/1997 | Bally et al. | |
| 5,596,086 A | 1/1997 | Matteucci et al. | |
| 5,596,091 A | 1/1997 | Switzer | |
| 5,597,696 A | 1/1997 | Linn et al. | |
| 5,597,909 A | 1/1997 | Urdea et al. | |
| 5,599,923 A | 2/1997 | Sessler et al. | |
| 5,599,928 A | 2/1997 | Hemmi et al. | |
| 5,602,240 A | 2/1997 | De Mesmaker et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci et al. | |
| 5,652,355 A | 7/1997 | Metelev et al. | |
| 5,652,356 A | 7/1997 | Agrawal | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,688,941 A | 11/1997 | Cook et al. | |
| 5,700,920 A | 12/1997 | Altmann et al. | |
| 5,700,922 A | 12/1997 | Cook | |
| 5,714,331 A | 2/1998 | Buchardt et al. | |
| 5,719,262 A | 2/1998 | Buchardt et al. | |
| 5,721,218 A | 2/1998 | Froehler | |
| 5,750,692 A | 5/1998 | Cook et al. | |
| 5,763,588 A | 6/1998 | Matteucci et al. | |
| 5,792,608 A | 8/1998 | Swaminathan et al. | |
| 5,792,747 A | 8/1998 | Schally et al. | |
| 5,801,154 A | 9/1998 | Baracchini et al. | |
| 5,830,653 A | 11/1998 | Froehler et al. | |
| 5,998,148 A * | 12/1999 | Bennett et al. | 435/6.11 |
| 6,005,096 A | 12/1999 | Matteucci et al. | |
| 6,007,992 A | 12/1999 | Lin et al. | |
| 6,028,183 A | 2/2000 | Lin et al. | |
| 6,043,060 A | 3/2000 | Imanishi | |
| 6,127,533 A | 10/2000 | Cook et al. | |
| 6,147,200 A | 11/2000 | Manoharan et al. | |

| | | | |
|---|---|---|---|
| 6,268,490 | B1 | 7/2001 | Imanishi et al. |
| 6,287,860 | B1 | 9/2001 | Monia et al. |
| 6,559,279 | B1 | 5/2003 | Manoharan et al. |
| 6,582,908 | B2 | 6/2003 | Fodor et al. |
| 6,670,461 | B1 | 12/2003 | Wengel et al. |
| 6,762,281 | B2 | 7/2004 | Manoharan et al. |
| 6,806,258 | B2 * | 10/2004 | Monia ............ 514/44 A |
| 6,887,906 | B1 | 5/2005 | Teng et al. |
| 7,250,289 | B2 * | 7/2007 | Zhou ............ 435/287.2 |
| 2001/0053519 | A1 | 12/2001 | Fodor et al. |
| 2002/0061530 | A1 * | 5/2002 | Belotserkovskii et al. ....... 435/6 |
| 2003/0027780 | A1 | 2/2003 | Hardee et al. |
| 2003/0158403 | A1 | 8/2003 | Manoharan et al. |
| 2003/0175906 | A1 | 9/2003 | Manoharan et al. |
| 2003/0207804 | A1 | 11/2003 | Manoharan et al. |
| 2003/0228597 | A1 | 12/2003 | Cowsert et al. |
| 2004/0138119 | A1 | 7/2004 | Tamm et al. |

OTHER PUBLICATIONS

GenBank Accession No. XM_131076.1, published by NCBI on Jan. 10, 2006 [retrieved on Feb. 13, 2010].*

Baker et al. (1997) J. Biol. Chem. 272(18):11994-2000.*

Stein, C.A., The Journal of Clinical Investigation vol. 108:641-644, 2001.*

Bennett et al., Biochimica et Biophysica Acta vol. 1489:19-30, 1999.*

U.S. Appl. No. 09/315,298, filed May 20, 1999, Teng et al.

Beasley et al., "Hepatocellular Carcinoma and Hepatitis B Virus: A Prospective Study of 22 707 Men in Taiwan " Lancet (1981) 2(8256):1129-1133.

Beaucage et al., "The Functionalization of Oligonucleotides Via Phosphoramidite Derivatives" Tetrahedron (1993) 49:1925-1963.

Berge et al., "Pharmaceutical Salts" J. of Pharma. Sci. (1977) 66:1-19.

Braasch et al., "Locked Nucleic Acid (LNA): fine-tuning the recognition of DNA and RNA" Chem. Biol. (2001) 8:1-7.

Braasch et al., "Novel Antisense and Peptide Nucleic Acid Strategies for Controlling Gene Expression" Biochemistry (2002) 41(14):4503-4510.

Braasch et al., "Antisense inhibition of gene expression in cells by oligonucleotides incorporating locked nucleic acids: effect of mRNA target sequence and chimera design." Nucleic Acids Research (2002) 30:5160-5167.

Branch et al., "A good antisense molecule is hard to find," TIBS (1998) 23:45-50.

Brazma, "Gene expression data analysis" FEBS Lett. (2000) 480:17-24.

Carulli et al., "High Throughput Analysis of Differential Gene Expression" J. Cell Biochem. Suppl. (1998) 31:286-296.

Celis et al., "Gene expression profiling: monitoring transcription and translation products using DNA microarrays and proteomics" FEBS Lett. (2000) 480:2-16.

Chaput et al., "DNA Polymerase-Mediated DNA Synthesis on a TNA Template" J. Am. Chem. Soc. (2003) 125:856-857.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Conte et al., "Conformational properties and thermodynamics of the RNA duplex r(CGCAAAUUUGCG)2: comparison with the DNA analogue d(CGCAAATTTGCG)2" Nucleic Acids Res. (1997) 25:2627-2634.

Crooke et al., "Basic Principles of Antisense Therapeutics" Antisense Research and Application (1998) Chapter 1:1-50.

Dellinger et al., "Solid-Phase Chemical Synthesis of Phosphonoacetate and Thiophosphonoacetate Oligodeoxynucleotides" J. Am. Chem. Soc. (2003) 125:940-950.

Egli et al., "RNA Hydration: A Detailed Look" Biochemistry (1996) 35:8489-8494.

Elayadi et al., "Application of PNA and LNA oligomers to chemotherapy" Curr. Opinion Invest. Drugs (2001) 2:558-561.

Englisch et al., "Chemically Modified Oligonucleotides as Probes and Inhibitors" Angewandte Chemie, International Edition (1991) 30:613-629.

Faira et al., "Phosphoramidate oligonucleotides as potent antisense molecules in cells and in vivo" Nat. Biotechnol. (2001) 19:40-44.

Fedoroff et al., "Structure of a DNA:RNA Hybrid Duplex: Why RNase H Does Not Cleave Pure RNA" J. Mol. Biol. (1993) 233:509-523.

Flanagan et al., "A cytosine analog that confers enhanced potency to antisense oligonucleotides" PNAS (1999) 96:3513-3518.

Fluiter et al., "In vivo tumor growth inhibition and biodistribution studies of locked nucleic acid (LNA) antisense oligonucleotides" Nucleic Acids Res. (2003) 31:953-962.

Frieden et al., "Expanding the design horizon of antisense oligonucleotides with alpha-L-LNA" Nucleic Acids Research (2003) 31(21):6365-6372.

Fuchs et al., "Identification of Differentially Expressed Genes by Mutually Subtracted RNA Fingerprinting" Anal. Biochem. (2000) 286:91-98.

Gait et al., "Applications of Chemically Synthesized RNA" RNA: Protein Interactions, Ed., Smith (1998) 1-36.

Gallo et al., "2'-C-Methyluridine phosphoramidite: a new building block for the preparation of RNA analogues carrying the 2'-hydroxyl group" Tetrahedron (2001) 57:5707-5713.

Going et al., "Molecular Pathology and Future Developments" Eur. J. Cancer (1999) 35(14):1895-1904.

Gonzalez et al., "Structure and Dynamics of a DNA-RNA Hybrid Duplex with a Chiral Phosphorothioate Moiety: NMR and Molecular Dynamics with Conventional and Time-Averaged Restraints" Biochemistry (1995) 34:4969-4982.

Gryaznov et al., "Oligodeoxyribonucleotide N3'->P5' Phosphoramidates: Synthesis and Hybridization Properties" J. Am. Chem. Soc. (1994) 116:3143-3144.

Guillerm et al., "Synthesis of 4'-Fluoroadenosine as an Inhibitor of S-Adenosyl-L-Homocysteine Hydrolase" Bioorganic and Medicinal Chemistry Letters (1995) 5(14):1455-1460.

Harry-O'Kura et al., "A Short, Flexible Route toward 2'-C-Branched Ribonucleosides" J. Org. Chem. (1997) 62(6):1754-1759.

Heasman, "Morpholino Oligos: Making Sense of Antisense?" J. Dev. Biol. (2002) 243:209-214.

Horton et al., "The Structure of an RNA/DNA Hybrid: A Substrate of the Ribonuclease Activity of HIV-1 Reverse Transcriptase" J. Mol. Biol. (1996) 264:521-533.

Hyrup "Peptide Nucleic Acids (PNA): Synthesis, Properties and Potential Applications" Bioorganic & Medicinal Chemistry (1996) 4(1):5-23.

Jacobson et al., "Methanocarba Analogues of Purine Nucleosides as Potent and Selective Adenosine Receptor Agonists" J. Med. Chem. Lett. (2000) 43:2196-2203.

Jungblut et al., "Proteom cs in human disease: Cancer, heart and infectious diseases" Electrophoresis (1999) 20:2100-2110.

Jurecic et al., "Long-distance DD-PCR and cDNA microarrays" Curr. Opin. Microbiol. (2000) 3:316-321.

Kawasaki et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. (1993) 36:831-841.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Koshkin et al., "LNA (Locked Nucleic Acid): An RNA Mimic Forming Exceedingly Stable LNA:LNA Duplexes" J. Am. Chem. Soc. (1998) 120:13252-13253.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Kurchavov et al., "A New Phosphoramidite Reagent for the Incorporation of Diazaphenoxazinone Nucleoside with Enhanced Base-Pairing Properties into Oligodeoxynucleotides" Nucleosides and Nucleotides (1997) 16(10&11):1837-1846.

Lacerra et al., "Restoration of hemoglobin A synthesis in erythroid cells from peripheral blood of thalassemic patients" PNAS (2000) 97:9591-9596.

Lane et al., "NMR assignments and solution conformation of the DNA-RNA hybrid duplex d(GTGAACTT)-r(AAGUUCAC)" Eur. J. Biochem. (1993) 215:297-306.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotechnol. (2000) 80:143-157.

Lee et al., "Ring-Constrained (N)-Methanocarba Nucleosides as Adenosine Receptor Agonists: Independent 5'-Uranamide and 2'-Deoxy Modifications" Bioorganic and Medicinal Chemistry Letters (2001) 11:1333-1337.

Lesnik et al., "Relative Thermodynamic Stability of DNA, RNA, and DNA:RNA Hybrid Duplexes: Relationship with Base Composition and Structure" Biochemistry (1995) 34:10807-10815.

Lin et al., "Tricyclic 2'-Deoxyctidine Analogs: Synthesis and Incorporation into Oligodeoxynucleotides Which Have Enhanced Binding to Complementary RNA" J. Am. Chem. Soc. (1995) 117:3873-3874.

Lin et al., "A Cytosine Analogue Capable of Clamp-Like Binding to a Guanine in Helical Nucleic Acids" J. Am. Chem. Soc. (1998) 120:8531-8532.

Madden et al., "Serial analysis of gene expression: from gene discovery to target identification" Drug Discov. Today (2000) 5:415-425.

Martin et al., "Ein neuer Zugang zu 2'-O-Alkylribonucleosiden and Eigenschaften deren Oligonucleotide" Helv. Chim. Acta (1995) 78:486-504.

Marusawa et al., "HBXIP functions as a cofactor of survivin in apoptosis suppression" EMBO J. (2003) 22(11):2729-2740.

McKay et al., "Characterization of a Potent and Specific Class of Antisense Oligonucleotide Inhibitor of Human Protein Kinase C-Expression" J. Biol. Chem. (1999) 274(3):1715-1722.

Melegari et al., "Cloning and Characterization of a Novel Hepatitis B Virus x Binding Protein That Inhibits Viral Replication " J. Virol (1998) 72(3):1737-1743.

Morita et al., "2'-O,4'-C-Ethylene-Bridged Nucleic Acids (ENA): Highly Nuclease-Resistant and Thermodynamically Stable Oligonucleotides for Antisense Drug" Bioorganic & Medicinal Chemistry Letters (2002) 12:73-76.

Morita et al., "Synthesis and Properties of 2'-0,4'-C-Ethylene-Bridged Nucleic Acids (ENA) as Effective Antisense Oligonucleotides" Bioorganic Medicinal Chemistry (2003) 11:2211-2226.

Murusawa et al., "HBXIP functions as a cofactor of survivin in apoptosis suppression" EMBO (2003) 22(11):2729-2740.

Nasevicius et al., "Effective targeted gene 'knockdown' in zebrafish" Nat. Genet. (2000) 26:216-220.

New England Biolabs 1998/99 Catalog (cover page and pp. 121 and 284).

Nielsen et al., "Sequence-Selective Recognition of DNA by Strand Displacement with a Thymine-Substituted Polyamide" Science (1991) 254:1497-1500.

Orum et al., "Locked nucleic acids: A promising molecular family for gene-function analysis and antisense drug development" Curr. Opinion Mol. Ther. (2001) 3:239-243.

Owen et al., "4'-Substituted Nucleosides. 3. Synthesis of Some 4'-Fluorouridine Derivatives" J. Org. Chem. (1976) 41:3010-3017.

Prashar et al., "READS: A Method for Display of 3'-End Fragments of Restriction Enzyme-Digested cDNAs for Analysis of Differential Gene Expression" Methods Enzymol. (1999) 303:258-272.

Reese et al., "An Acetal Group Suitable for the Protection of 2'-Hydroxy Functions in Rapid Oligoribonucleotide Synthesis" Tetrahedron Lett. (1986) 27:2291.

Renneberg et al., "Antisense properties of tricyclo-DNA" Nucleic Acids Res. (2002) 30(13):2751-2757.

Renneberg et al., "Watson-Crick Base-Pairing Properties of Tricyclo-DNA" J. Am. Chem. Soc. (2002) 124:5993-6002.

Reynolds et al., "Rational siRNA design for RNA interference" Nature Biotechnology (2004) 22(3):326-330.

Sanghvi et al., "Antisense oligodeoxynucleotides; synthesis, biophysical and biological evaluation of oligodeoxynucleotides containing modified pyrimidines" Nucleic Acids Research (1993) 21(14):3197-3203.

Sanghvi et al., "Heterocyclic Base Modifications in Nucleic Acids and Their Applications in Antisense Oligonucleotides" Antisense Research and Applications (1993) pp. 273-288.

Sazani et al., "Systemically delivered antisense oligomers upregulate gene expression in mouse tissues" Nat. Biotechnol. (2002) 20:1228-1233.

Scaringe, "RNA Oligonucleotide Synthesis via 5'-Silyl-2'-Orthoester Chemistry" Methods (2001) 23:206-217.

Schwartz et al., "Rapid Synthesis of Oligoribonucleotides Using 2'-O-(o-Nitrobenzyloxymethyl)-Protected Monomers" Bioorg. Med. Chem. Lett. (1992) 2(9):1019-1024.

Searle et al., "On the stability of nucleic acid structures in solution: enthalpy-entropy compensations, internal rotations and reversibility" Nucleic Acids Res. (1993) 21(9):2051-2056.

Sheehan et al., "Biochemical properties of phosphonoacetate and thiophosphonoacetate oligodeoxyribonucleotides" Nucleic Acids Research (2003) 31(14):4109-4118.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63:10035-10039.

Skorski et al., "Antileukemia effect of c-myc N3'->P5' phosphoramidate antisense oligonucleotides in vivo" Proc. Natl. Acad. Sci. (1997) 94:3966-3971.

Steffens et al., "Nucleic-Acid Analogs with Constraint Conformationally Flexibility in the Sugar-Phosphate Backbone 'Tricyclo-DNA' Part 1" Helv. Chim. Acta. (1997) 80:2426-2439.

Steffens et al., "Synthesis and Thermodynamic and Biophysical Properties of Tricyclo-DNA" J. Am. Chem. Soc. (1999) 121(14):3249-3255.

Sutcliffe et al., "TOGA: An automated parsing technology for analyzing expression of nearly all genes" PNAS (2000) 97:1976-1981.

Tang et al., "2'-C-Branched Ribonucleosides: Synthesis of the Phosphoramidite Derivatives of 2'-C-Beta-Methylcytidine and their Incorporation into Oligonucleotides" J. Org. Chem. (1999) 64:747-754.

To, "Identification of Differential Gene Expression by High Throughput Analysis" Comb. Chem. High Throughput Screen (2000) 3:235-241.

Wahlestedt et al., "Potent and nontoxic antisense oligonucleotides containing locked nucleic acids" Proc. Natl. Acad. Sci. (2000) 97(10):5633-5638.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122:8595-8602.

Wang et al., "Synthesis and binding property of an oligonucleotide containing tetrafluorophenoxazine" Tetrahedron Lett. (1998) 39:8385-8388.

Wu et al., "Base-Pairing Systems Related to TNA: alpha-Threofuranosyl Oligonucleotides Containing Phosphoramidate Linkages" Organic Letters (2002) 4(8):1279-1282.

The Concise Encyclopedia of Polymer Science and Engineering, Kroschwitz ed., John Wiley & Sons, 1990, pp. 858-859.

International Search Report for Application No. PCT/US07/73799 dated Jul. 18, 2007.

* cited by examiner

US 8,198,253 B2

COMPOSITIONS AND THEIR USES DIRECTED TO HBXIP

CROSS REFERENCE TO RELATED APPLICATIONS

This application is a U.S. National Stage application of International Application No. PCT/US2007/073799, filed 18 Jul. 2007, which claims the priority benefit of U.S. Patent Application No. 60/807,803 filed 19 Jul. 2006, the contents of which are incorporated herein by reference in their entirety.

INCORPORATION OF SEQUENCE LISTING

The present application is being filed along with a Sequence Listing in electronic format. The Sequence Listing is provided as a file entitled BIOL0064WO, created on Jul. 17, 2007 which is 48 Kb in size. The information in the electronic format of the sequence listing is incorporated herein by reference in its entirety.

FIELD OF THE INVENTION

Disclosed herein are compounds, compositions and methods for modulating the expression of HBXIP in a cell, tissue or animal.

BACKGROUND OF THE INVENTION

Chronic hepatitis B virus (HBV) infection affects over 400 million people worldwide and is associated with a 100- to 200-fold greater risk of developing hepatocellular carcinoma (HCC) (Melegari et al. (1998) J. Virol. 72(3):1737-1743; Beasley et al. (1981) Lancet 2:1129-1133). HBV, as well as other mammalian hepadnaviruses, contains a highly conserved open reading frame encoding the HBV x protein (HBx). HBx is required to establish a productive infection in the liver and is known to function as an activator of mitogenic pathways and as a transcriptional transactivator. The ability of HBx to alter signaling pathways involved in cellular growth and differentiation and apoptosis suggested a role for HBx in the development of HCC in the livers of persistently infected patients (Melegari et al. (1998) J. Virol. 72(3):1737-1743).

Hepatitis B X-interacting protein (HBXIP) was first identified as a cellular protein that interacts with HBx. Expression of HBXIP is observed in nearly all tissues, not just the liver (Melegari et al. (1998) J. Virol. 72(3):1737-1743). Elevated levels of HBXIP have been found in both cancerous and non-malignant liver tissue of humans with chronic HBV infection, relative to normal hepatic tissue. Little is known about the role of HBXIP; however, HBXIP has been shown to interact with survivin, an anti-apoptotic protein that is overexpressed in most types of human cancer (Marusawa et al. (2003) EMBO J. 22(11):2729-2740). Survivin normally plays an essential role in chromosome segregation and cytokinesis during cell division. When survivin is overexpressed, such as in tumors, it manifests an anti-apoptotic role. Marusawa et al. demonstrate that survivin forms a complex with HBXIP and that these complexes inhibit apoptosis by binding to pro-caspase 9, which prevents its recruitment to Apaf1, thus halting the apoptotic pathway. Neither survivin nor HBXIP alone were capable of preventing apoptosis, suggesting that HBXIP functions as a survivin co-factor. This study suggests that HBx regulates apoptotic pathways during viral infection via HBXIP and survivin and points to HBXIP as an important factor in the development of HCC and other types of cancer.

U.S. pre-grant publication 2004-0138119 discusses inhibiting interaction of survivin and HBXIP to modulate apoptosis. Disclosed methods of inhibiting interaction include survivin- or HBXIP-specific antibodies, molecular decoys, specific inhibitors, antisense and siRNAs.

Little is known about the cellular functions of HBXIP and how it contributes to the development of HCC and other types of cancer. However, HBXIP appears to influence apoptotic pathways, making it an excellent target for anti-cancer therapeutics. Thus, there remains a significant need for specific inhibitors of HBXIP.

SUMMARY OF THE INVENTION

Provided herein are oligomeric compounds targeted to a nucleic acid encoding HBXIP. In one embodiment, the oligomeric compounds are antisense compounds which modulate the expression of HBXIP. In another embodiment, the antisense compounds are modified antisense oligonucleotides.

Provided are antisense oligonucleotides 13 to 80 nucleobases in length with a first region comprising one or more deoxynucleotides and second and third regions flanking the first region, each comprising at least one 2'-O-(2-methoxyethyl) nucleotide, wherein the oligonucleotide specifically hybridizes with HBXIP and inhibits expression of HBXIP. In one embodiment, the antisense oligonucleotide is 13 to 50 nucleobase in length. In another embodiment, the antisense oligonucleotide is 13 to 30 nucleobases in length. In another embodiment, the antisense oligonucleotide is 20 to 30 nucleobases in length. In another embodiment, the antisense oligonucleotide is 20 nucleobases in length. In one embodiment, HBXIP is human HBXIP. In another embodiment, HBXIP is mouse HBXIP.

Also provided are antisense oligonucleotides 20 nucleotides in length with a first region comprising 10 deoxynucleotides flanked by second and third regions comprising five 2'-O-(2-methoxyethyl) nucleotides. In one embodiment, the antisense oligonucleotides further comprise a modified internucleoside linkage at each position. In one embodiment, the modified internucleoside linkage is a phosphorothioate. Also provided are antisense oligonucleotides comprising a modified nucleobase. In one embodiment, the modified nucleobase is a 5-methyl cytosine.

Also provided are methods of inducing apoptosis of cancer cells, comprising contacting cancer cells with an antisense oligonucleotide 13 to 80 nucleobases in length with a first region comprising one or more deoxynucleotides and second and third regions flanking the first region, each comprising at least one 2'-O-(2-methoxyethyl) nucleotide such that apoptosis is induced. In one embodiment, the cells are derived from the liver. In another embodiment, the cells are infected with HBV.

Further provided are methods of inhibiting expression of HBXIP in cells or tissues, comprising contacting the cells or tissues with an antisense oligonucleotide 13 to 80 nucleobases in length with a first region comprising one or more deoxynucleotides and second and third regions flanking the first region, each comprising at least one 2'-O-(2-methoxyethyl) nucleotide such that expression of HBXIP is inhibited. In one embodiment, the cells or tissues are derived from the liver.

Also provided are methods of inhibiting hepatocellular carcinoma tumor growth in an animal, comprising selecting an animal with hepatocellular carcinoma and administering to the animal an antisense oligonucleotide 13 to 80 nucleobases in length with a first region comprising one or more deoxynucleotides and second and third regions flanking the first region, each comprising at least one 2'-O-(2-methoxyethyl) nucleotide.

Also contemplated are antisense compounds comprising a stretch of at least eight consecutive nucleobases selected from within the illustrative antisense compounds or antisense compounds comprising a stretch of at least thirteen consecutive nucleobases selected from within the illustrative antisense compounds.

DETAILED DESCRIPTION OF THE INVENTION

Antisense technology is an effective means for reducing the expression of one or more specific gene products and is uniquely useful in a number of therapeutic, diagnostic, and research applications. Provided herein are antisense compounds useful for modulating gene expression and associated pathways via antisense mechanisms of action based on target degradation or target occupancy.

The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

HBXIP is a cellular gene first identified as interacting with the X protein of HBV. Studies of HBXIP have implicated it in the regulation of apoptosis and as a contributing factor to the development of HCC, particularly HCC resulting from chronic HBV infection. The exact cellular functions of HBXIP are still unclear, but HBXIP may contribute to a variety of different malignancies by interacting with survivin to suppress apoptosis. Thus, there is a great need for the development of specific HBXIP inhibitors. Disclosed herein are oligomeric compounds, including antisense oligonucleotides and other antisense compounds for use in modulating the expression of nucleic acid molecules encoding HBXIP. This is accomplished by providing oligomeric compounds which hybridize with one or more target nucleic acid molecules encoding HBXIP.

As used herein, the terms "target nucleic acid" and "nucleic acid molecule encoding HBXIP" have been used for convenience to encompass DNA encoding HBXIP, RNA (including pre-mRNA and mRNA or portions thereof) transcribed from such DNA, and also cDNA derived from such RNA.

As used herein, "targeting" or "targeted to" refer to the process of designing an oligomeric compound such that the compound hybridizes with a selected nucleic acid molecule.

As used herein, "hybridization" means the pairing of complementary strands of oligomeric compounds. In the context of the present invention, an oligomeric compound is specifically hybridizable when there is a sufficient degree of complementarity to avoid non-specific binding of the oligomeric compound to non-target nucleic acid sequences.

As used herein, "antisense mechanisms" are all those involving hybridization of a compound with target nucleic acid, wherein the outcome or effect of the hybridization is either target degradation or target occupancy with concomitant stalling of the cellular machinery involving, for example, transcription or splicing.

In accordance with the present invention are compositions and methods for modulating the expression of HBXIP (also known as hepatitis B virus x-interacting protein (9.6 kD); HBx-interacting protein; and XIP). Listed in Table 1 are GENBANK® accession numbers of sequences used to design oligomeric compounds targeted to HBXIP. Oligomeric compounds of the invention include oligomeric compounds which hybridize with one or more target nucleic acid molecules shown in Table 1, as well as oligomeric compounds which hybridize to other nucleic acid molecules encoding HBXIP. The oligomeric compounds may target any region, segment, or site of nucleic acid molecules which encode HBXIP. Suitable target regions, segments, and sites include, but are not limited to, the 5'UTR, the start codon, the stop codon, the coding region, the 3'UTR, the 5'cap region, introns, exons, intron-exon junctions, exon-intron junctions, and exon-exon junctions.

TABLE 1

Gene Targets

| Species | Genbank # | SEQ ID NO: |
|---|---|---|
| Human | NM_006402.2 | 1 |
| Human | the complement of nucleotides 7029594 to 7037061 of NT_019273.17 | 2 |
| Mouse | BY282117.1 | 3 |
| Mouse | nucleotides 9030000 to 9036000 of NT_039239.2 | 4 |
| Mouse | XM_131076.1 | 5 |

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds in accordance with this invention comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 10 to 50 nucleobases. One having ordinary skill in the art will appreciate that this embodies antisense compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases.

In one embodiment, the antisense compounds of the invention comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 50 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention comprise 13 to 30 nucleobases. One having ordinary skill in the art will appreciate that this embodies antisense compounds of 13, 14, 15, 16, 17, 18, 19, 20, 21, 22, 23, 24, 25, 26, 27, 28, 29 or 30 nucleobases.

In some embodiments, the antisense compounds of the invention comprise 15 to 30 nucleobases. One having ordinary skill in the art will appreciate that this embodies antisense compounds of 15, 16, 17, 18, 19, 20, 21, 22, 23, 24, 25, 26, 27, 28, 29 or 30 nucleobases.

In one embodiment, the antisense compounds of the invention comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds of the invention comprise 20 to 24 nucleobases. One having ordinary skill in the art will appreciate that this embodies antisense compounds of 20, 21, 22, 23, or 24 nucleobases.

In one embodiment, the antisense compounds of the invention comprise 20 nucleobases.

In one embodiment, the antisense compounds of the invention comprise 19 nucleobases.

In one embodiment, the antisense compounds of the invention comprise 18 nucleobases.

In one embodiment, the antisense compounds of the invention comprise 17 nucleobases.

In one embodiment, the antisense compounds of the invention comprise 16 nucleobases.

In one embodiment, the antisense compounds of the invention comprise 15 nucleobases.

In one embodiment, the antisense compounds of the invention comprise 14 nucleobases.

In one embodiment, the antisense compounds of the invention comprise 13 nucleobases.

Antisense compounds 8-80 nucleobases in length comprising a stretch of at least eight (8) consecutive nucleobases selected from within the illustrative antisense compounds are considered to be suitable antisense compounds. Antisense compounds 13-80 nucleobases in length comprising a stretch of at least thirteen (13) consecutive nucleobases selected from within the illustrative antisense compounds also are considered to be suitable antisense compounds.

Compounds of the invention include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 to about 80 nucleobases.

Compounds of the invention also include oligonucleotide sequences that comprise at least the 13 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 13 to about 80 nucleobases). Other compounds are represented by oligonucleotide sequences that comprise at least the 13 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 13 to about 80 nucleobases). It is also understood that compounds may be represented by oligonucleotide sequences that comprise at least 13 consecutive nucleobases from an internal portion of the sequence of an illustrative compound, and may extend in either or both directions until the oligonucleotide contains about 13 to about 80 nucleobases.

One having skill in the art armed with the antisense compounds illustrated herein will be able, without undue experimentation, to identify further antisense compounds.

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refer to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

The oligomeric compounds of the invention also include compounds in which a different base is present at one or more of the nucleotide positions in the compound. For example, if the first nucleotide is an adenosine, compounds may be produced which contain thymidine, guanosine or cytidine at this position. This may be done at any of the positions of the oligomeric compound. These compounds are then tested using the methods described herein to determine their ability to inhibit expression of HBXIP mRNA.

As used herein, "targeting" or "targeted to" refer to the process of designing an oligomeric compound such that the compound hybridizes with a selected nucleic acid molecule. Targeting an oligomeric compound to a particular target nucleic acid molecule can be a multistep process. The process usually begins with the identification of a target nucleic acid whose expression is to be modulated. As used herein, the terms "target nucleic acid" and "nucleic acid encoding HBXIP" encompass DNA encoding HBXIP, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes HBXIP.

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Target regions may include, for example, a particular exon or intron, or may include only selected nucleobases within an exon or intron which are identified as appropriate target regions. Within regions of target nucleic acids are segments. "Segments" are defined as smaller or sub-portions of regions within a target nucleic acid. "Sites," as used in the present invention, are defined as unique nucleobase positions within a target nucleic acid. As used herein, the "target site" of an oligomeric compound is the 5'-most nucleotide of the target nucleic acid to which the compound binds.

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5' CUG, and 5' AUA, 5' ACG and 5' CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. "Start codon" and "translation initiation codon" refer to the codon or codons that are used in vivo to initiate translation of an mRNA transcribed from a gene encoding a protein, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with oligomeric compounds of the invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product are implicated in disease, or where aberrant levels of an aberrant splice product are implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Consequently, the types of variants described herein are also suitable target nucleic acids.

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Specific examples of oligomeric compounds useful of the present invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds can have one or more modified internucleoside linkages. Modified oligonucleotide backbones containing a phosphorus atom therein include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage, i.e., a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Oligomeric compounds may also contain one or more substituted sugar moieties. Suitable compounds can comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O-$CH_2CH_2OCH_3$, also known as 2'-O-(2-methoxyethyl) or 2'-MOE) (Martin et al., Helv. Chim. Acta, 1995, 78, 486-504), i.e., an alkoxyalkoxy group. A further modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2-O-dimethyl-amino-ethoxy-ethyl or 2'-DMAEOE), i.e., 2'-O—$(CH_2)_2$—O—$(CH_2)_2$—$N(CH_3)_2$, also described in examples hereinbelow.

Other modifications include 2'-methoxy (2'-O—$CH_3$), 2'-aminopropoxy (2'-O$CH_2CH_2CH_2NH_2$), 2'-allyl (2-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

The terms used to describe the conformational geometry of homoduplex nucleic acids are "A Form" for RNA and "B Form" for DNA. In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger et al., Principles of Nucleic Acid Structure, 1984, Springer-Verlag; New York, N.Y.). As used herein, B-form geometry is inclusive of both C2'-endo pucker and O4'-endo pucker.

The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). Consequently, compounds that favor an A-form geometry can enhance stacking interactions, thereby increasing the relative Tm and potentially enhancing a compound's antisense effect.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA-like nucleosides so that particular properties of an oligomeric compound can be enhanced while maintaining the desirable 3'-endo conformational geometry.

There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. Also provided herein are oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Representative 2'-substituent groups amenable to the present invention that give A-form conformational properties (3'-endo) to the resultant duplexes include 2'-O-alkyl, 2'-O-substituted alkyl and 2'-fluoro substituent groups. Other suitable substituent groups are various alkyl and aryl ethers and thioethers, amines and monoalkyl and dialkyl substituted amines.

Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

The synthesis of numerous of the modified nucleosides amenable to the present invention are known in the art (see for example, Chemistry of Nucleosides and Nucleotides Vol 1-3, ed. Leroy B. Townsend, 1988, Plenum press). The conformation of modified nucleosides and their oligomers can be estimated by various methods routine to those skilled in the art such as molecular dynamics calculations, nuclear magnetic resonance spectroscopy and CD measurements.

Another group of oligomeric compounds includes oligonucleotide mimetics. The term "mimetic" as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA) (Nielsen et al., Science, 1991, 254, 1497-1500). PNAs have favorable hybridization properties, high biological stability and are electrostatically neutral molecules. PNA compounds have been used to correct aberrant splicing in a transgenic mouse model (Sazani et al., Nat. Biotechnol., 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. Morpholino-based oligomeric compounds are non-ionic mimetics of oligonucleotides which are less likely to form undesired interactions with cellular proteins (Dwaine A. Braasch and David R. Corey, Biochemistry, 2002, 41(14), 4503-4510). Morpholino-based oligomeric compounds have been studied in zebrafish embryos (see: Genesis, volume 30, issue 3, 2001 and Heasman, J., Dev. Biol., 2002, 243, 209-214). Further studies of morpholino-based oligomeric compounds have also been reported (Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N(CH$_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). In CeNA oligonucleotides, the furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase H resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., *Curr. Opinion Invens. Drugs*, 2001, 2, 558-561; Braasch et al., *Chem. Biol.*, 2001, 8 1-7; and Orum et al., *Curr. Opinion Mol. Ther.*, 2001, 3, 239-243; see also U.S. Pat. Nos. 6,268,490 and 6,670,461). The linkage can be a methylene (—$CH_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., *Bioorganic Medicinal Chemistry*, 2003, 11, 2211-2226). LNA and other bicyclic sugar analogs display very high duplex thermal stabilities with complementary DNA and RNA (Tm=+3 to +10° C.), stability towards 3'-exonucleolytic degradation and good solubility properties. LNA's are commercially available from ProLigo (Paris, France and Boulder, Colo., USA).

An isomer of LNA that has also been studied is alpha-L-LNA which has been shown to have superior stability against a 3'-exonuclease. The alpha-L-LNA's were incorporated into antisense gapmers and chimeras that showed potent antisense activity (Frieden et al., *Nucleic Acids Research*, 2003, 21, 6365-6372).

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11° C.) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA LNA chimeras have been shown to efficiently inhibit gene expression when targeted to a variety of regions (5'-untranslated region, region of the start codon or coding region) within the luciferase mRNA (Braasch et al., *Nucleic Acids Research*, 2002, 30, 5160-5167).

Potent and nontoxic antisense oligonucleotides containing LNAs have been described (Wahlestedt et al., *Proc. Natl. Acad. Sci. U.S.A.*, 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., *Proc. Natl. Acad. Sci.*, 2000, 97, 5633-5638) and in another study showed a blockage of the translation of the large subunit of RNA polymerase II (Fluiter et al., *Nucleic Acids Res.*, 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in *Chemical and Engineering News*, 2003, 81, 9). In another study it was determined that TNA is capable of antiparallel Watson-Crick base pairing with complementary DNA, RNA and TNA oligonucleotides (Chaput et al., *J. Am. Chem. Soc.*, 2003, 125, 856-857).

In one study (3',2')-alpha-L-threose nucleic acid was prepared and compared to the 2' and 3' amidate analogs (Wu et al., *Organic Letters*, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., *Helv. Chim. Acta*, 1997, 80, 2426-2439; Steffens et al., *J. Am. Chem. Soc.*, 1999, 121, 3249-3255; Renneberg et al., *J. Am. Chem. Soc.*, 2002, 124, 5993-6002; and Renneberg et al., *Nucleic acids res.*, 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Oligomeric compounds can also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). A "substitution" is the replacement of an unmodified or natural base with another unmodified or natural base. "Modified" nucleobases mean other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3 H)-one), phenothiazine cytidine (1 H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deaza-guanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are known to those skilled in the art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications. It is understood in the art that modification of the base does not entail such chemical modifications as to produce substitutions in a nucleic acid sequence.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941; and 5,750,692.

Oligomeric compounds of the present invention can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one (Kurchavov, et al., *Nucleosides and Nucleotides*, 1997, 16, 1837-1846), 1,3-diazaphenothiazine-2-one, (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Pre-Grant Publications 20030207804 and 20030175906).

Further helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° C. relative to 5-methyl cytosine (dC5$^{me}$), which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Pre-Grant Publication 20030158403.

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5'cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270). For siRNA constructs, the 5' end (5' cap) is commonly but not limited to 5'-hydroxyl or 5'-phosphate.

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single-or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxynucleotide gap flanked by five non-deoxynucleotide wings. This is referred to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-N$^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, (5'-O-(4,4'-Dimethoxytriphenylmethyl)-2'-O-(2-methoxyethyl)-N$^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N$^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-N$^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O-(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., *Nucleic Acids Research*, 1993, 21, 3197-3203) using commercially available phosphoramidites (Glen Research, Sterling VA or Chem-Genes, Needham, Mass.).

2'-fluoro oligonucleotides can be synthesized routinely as described (Kawasaki, et. al., *J. Med. Chem.*, 1993, 36, 831-841) and U.S. Pat. No. 5,670,633.

2'-O-Methoxyethyl-substituted nucleoside amidites can be prepared routinely as per the methods of Martin, P., *Helvetica Chimica Acta*, 1995, 78, 486-504.

Aminooxyethyl and dimethylaminooxyethyl amidites can be prepared routinely as per the methods of U.S. Pat. No. 6,127,533.

Phosphorothioate-containing oligonucleotides (P=S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. Nos. 5,610,289 or 5,625,050.

Phosphoramidite oligonucleotides can be prepared as described in U.S. Pat. Nos. 5,256,775 or 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Peptide nucleic acids (PNAs) can be prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, 5,719,262, 6,559,279 and 6,762,281.

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound.

A large number of 2'-O-protecting groups have been used for the synthesis of oligoribo-nucleotides and any can be used. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese et al. have identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach is to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group, initially used for the synthesis of oligoribonucleotides, is the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal. For example, the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—CH$_2$—O—Si(iPr)$_3$, TOM). One 2'-O-protecting group that was prepared to be used orthogonally to the TOM group was 2'-O-[(R)-1-(2-nitrophenyl)ethyloxy)methyl]((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

The main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl](FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

(2'-O-Me)-(2'-deoxy)-(2'-O-Me) Chimeric Phosphorothioate Oligonucleotides

Chimeric oligonucleotides having 2'-O-alkyl phosphorothioate and 2'-deoxy phosphorothioate oligonucleotide segments can be routinely synthesized by one skilled in the art, using, for example, an Applied Biosystems automated DNA synthesizer Model 394. Oligonucleotides can be synthesized using an automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. In one nonlimiting example, the standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligonucleotide is then recovered by an appropriate method (precipitation, column chromatography, volume reduced in vacuo) and analyzed by methods routine in the art.

(2'-O-(2-Methoxyethyl))-(2'-deoxy)-(2'-O-(2-Methoxyethyl)) Chimeric Phosphorothioate Oligonucleotides (2'-O-(2-methoxyethyl))-(2'-deoxy)-(-2'-O-(2-methoxyethyl)) chimeric phosphorothioate oligonucleotides can be prepared as per the procedure above for the 2'-O-methyl chimeric oligonucleotide, with the substitution of 2'-O-(methoxyethyl)amidites for the 2'-O-methyl amidites.

(2'-O-(2-Methoxyethyl)Phosphodiester)-(2'-deoxy Phosphorothioate)-(2'-O-(2-Methoxyethyl) Phosphodiester) Chimeric Oligonucleotides (2'-O-(2-methoxyethyl phosphodiester)-(2'-deoxy phosphorothioate)-(2'-O-(methoxyethyl)phosphodiester) chimeric oligonucleotides can be prepared as per the above procedure for the 2'-O-methyl chimeric oligonucleotide with the substitution of 2'-O-(methoxyethyl)amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides can be synthesized according to U.S. Pat. No. 5,623,065.

Methods of oligonucleotide purification and analysis are known to those skilled in the art. Analysis methods include capillary electrophoresis (CE) and electrospray-mass spectroscopy. Such synthesis and analysis methods can be performed in multi-well plates.

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of HBXIP. Thus, in one embodiment modulation of expression can mean increase or decrease in target RNA or protein levels. In another embodiment modulation of expression can mean an increase or decrease of one or more RNA splice products, or a change in the ratio of two or more splice products.

Modulation of HBXIP expression can be assayed in a variety of ways known in the art. HBXIP mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by HBXIP can be quantitated in a variety of ways well known in the art, such as immunoprecipitation, Western blot analysis (immunoblotting), ELISA or fluorescence-activated cell sorting (FACS). Antibodies directed to a protein encoded by HBXIP can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Once one or more target regions, segments or sites have been identified, oligomeric compounds are designed which are sufficiently complementary to the target, i.e., hybridize sufficiently well and with sufficient specificity, to give the desired effect. The oligomeric compounds of the present invention can be targeted to features of a target nucleobase sequence, such as those described in Table 1.

The locations on the target nucleic acid to which active oligomeric compounds hybridize are hereinbelow referred to as "validated target segments." As used herein the term "validated target segment" is defined as at least an 8-nucleobase portion, or at least a 13-nucleobase portion, of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 8 to about 80 nucleobases). Similarly validated target segments are represented by DNA or RNA sequences that comprise at least the 8 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 8 to about 80 nucleobases). It is also understood that a validated oligomeric target segment can be represented by DNA or RNA sequences that comprise at least 8 consecutive nucleobases from an internal portion of the sequence of a validated target segment, and can extend in either or both directions until the oligonucleotide contains about 8 about 80 nucleobases.

Target segments can also include DNA or RNA sequences that comprise at least the 13 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 13 to about 80 nucleobases). Similarly validated target segments are represented by DNA or RNA sequences that comprise at least the 13 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 13 to about 80 nucleobases). It is also understood that a validated oligomeric target segment can be represented by DNA or RNA sequences that comprise at least 13 consecutive nucleobases from an internal portion of the sequence of a validated target segment, and can extend in either or both directions until the oligonucleotide contains about 13 to about 80 nucleobases.

In another embodiment, the validated target segments identified herein can be employed in a screen for additional compounds that modulate the expression of HBXIP. "Modulators" are those compounds that modulate the expression of HBXIP and which comprise at least an 8-nucleobase portion which is complementary to a validated target segment. The screening method comprises the steps of contacting a validated target segment of a nucleic acid molecule encoding HBXIP with one or more candidate modulators, and selecting for one or more candidate modulators which perturb the expression of a nucleic acid molecule encoding HBXIP. Once it is shown that the candidate modulator or modulators are capable of modulating the expression of a nucleic acid molecule encoding HBXIP, the modulator can then be employed in further investigative studies of the function of HBXIP, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

The oligomeric compounds of the present invention can be utilized for diagnostics, therapeutics, prophylaxis and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions of the present invention are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SURF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Compounds of the invention can be used to modulate the expression of HBXIP in an animal, such as a human. In one non-limiting embodiment, the methods comprise the step of administering to said animal an effective amount of an antisense compound that inhibits expression of HBXIP. In one embodiment, the antisense compounds of the present invention effectively inhibit the levels or function of HBXIP RNA. Because reduction in HBXIP mRNA levels can lead to alteration in HBXIP protein products of expression as well, such resultant alterations can also be measured. Antisense compounds of the present invention that effectively inhibit the levels or function of HBXIP RNA or protein products of expression is considered an active antisense compound. In one embodiment, the antisense compounds of the invention inhibit the expression of HBXIP causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of HBXIP can be measured in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The cells contained within said fluids, tissues or organs being analyzed can contain a nucleic acid molecule encoding HBXIP protein and/or the HBXIP-encoded protein itself. For example, fluids, tissues or organs procured from an animal can be evaluated for expression levels of the target mRNA or protein. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the target gene expression in the aforementioned fluids, tissues or organs, collected from an animal contacted with one or more compounds of the invention, by routine clinical methods known in the art.

These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

The compounds of the present invention can be utilized in pharmaceutical compositions by adding an effective amount of a compound to a suitable pharmaceutically acceptable diluent or carrier. In one aspect, the compounds of the present invention inhibit the expression of HBXIP. The compounds of the invention can also be used in the manufacture of a medicament for the treatment of diseases and disorders related to HBXIP expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of HBXIP expression in the cells of bodily fluids, organs or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

The oligomeric compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 22 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts of antisense oligonucleotides are useful and are well accepted for therapeutic administration to humans. In another embodiment, sodium salts of dsRNA compounds are also provided.

The oligomeric compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including but not limited to ophthalmic and to mucous membranes including vaginal and rectal delivery), pulmonary, e.g., by inhalation or insufflation of powders or aerosols, including by nebulizer (intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Sites of administration are known to those skilled in the art. Oligonucleotides with at least one 2'-O-methoxyethyl modification are believed to be useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Formulations for topical administration include those in which the oligomeric compounds of the invention are in admixture with a topical delivery agent such as lipids, liposomes, fatty acids, fatty acid esters, steroids, chelating agents and surfactants.

For topical or other administration, oligomeric compounds of the invention may be encapsulated within liposomes or may form complexes thereto, such as to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to affect the efficient delivery of oligomeric compounds, particularly oligonucleotides. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property.

Oral compositions for administration of non-parenteral oligomeric compounds can be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. Such oral oligomeric compound compositions can be referred to as "mucosal penetration enhancers."

Oligomeric compounds, such as oligonucleotides, may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002.

In one embodiment, oral oligomeric compound compositions comprise at least one member of the group consisting of surfactants, fatty acids, bile salts, chelating agents, and non-chelating surfactants. Further embodiments comprise oral oligomeric compound comprising at least one fatty acid, e.g. capric or lauric acid, or combinations or salts thereof. One combination is the sodium salt of lauric acid, capric acid and UDCA.

In one embodiment, oligomeric compound compositions for oral delivery comprise at least two discrete phases, which phases may comprise particles, capsules, gel-capsules, microspheres, etc. Each phase may contain one or more oligomeric compounds, penetration enhancers, surfactants, bioadhesives, effervescent agents, or other adjuvant, excipient or diluent A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Oral oligomeric compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers.

One of skill in the art will recognize that formulations are routinely designed according to their intended use, i.e. route of administration.

Compositions of the invention can contain two or more oligomeric compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially.

While certain compounds, compositions and methods of the present invention have been described with specificity in accordance with certain embodiments, the following examples serve only to illustrate the compounds of the invention and are not intended to limit the same. Each of the references, GENBANK® accession numbers, and the like recited in the present application is incorporated herein by reference in its entirety.

EXAMPLE 1

Cell Types

The effect of oligomeric compounds on target nucleic acid expression was tested in one or more of the following cell types.

T-24 Cells

The transitional cell bladder carcinoma cell line T-24 was obtained from the American Type Culture Collection (ATCC) (Manassas, Va.). T-24 cells are routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the compounds of the invention.

b.END Cells

The mouse brain endothelial cell line b.END was obtained from Dr. Werner Risau at the Max Plank Institute (Bad Nauheim, Germany). b.END cells are routinely cultured in DMEM, high glucose (Gibco/Life Technologies, Gaithersburg, Md.) supplemented with 10% fetal calf serum (Gibco/Life Technologies, Gaithersburg, Md.). Cells are routinely passaged by trypsinization and dilution when they reach 90% confluence. Cells are seeded into 96-well plates (Falcon-Primaria #3872) at a density of 3000 cells/well for treatment with the oligomeric compounds of the invention.

Treatment with Oligomeric Compounds

When cells reach appropriate confluency, they are treated with oligonucleotide using a transfection method as described.

LIPOFECTIN™

When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

Control Oligonucleotides

Control oligonucleotides are used to determine the optimal oligomeric compound concentration for a particular cell line. Furthermore, when oligomeric compounds of the invention are tested in oligomeric compound screening experiments or phenotypic assays, control oligonucleotides are tested in parallel with compounds of the invention. In some embodiments, the control oligonucleotides are used as negative control oligonucleotides, i.e., as a means for measuring the absence of an effect on gene expression or phenotype. In alternative embodiments, control oligonucleotides are used as positive control oligonucleotides, i.e., as oligonucleotides known to affect gene expression or phenotype. Control oligonucleotides are shown in Table 2. "Target Name" indicates the gene to which the oligonucleotide is targeted. "Species of Target" indicates species in which the oligonucleotide is perfectly complementary to the target mRNA. "Motif" is indicative of chemically distinct regions comprising the oligonucleotide. The compounds in Table 2 are chimeric oligonucleotides, composed of a central "gap" region consisting of 2'-deoxynucleotides, which is flanked on both sides (5' and 3') by "wings". The wings are composed of 2'-O-(2-methoxyethyl) nucleotides, also known as 2'-MOE nucleotides. The "motif" of each gapmer oligonucleotide is illustrated in Table 2 and indicates the number of nucleotides in each gap region and wing, for example, "5-10-5" indicates a gapmer having a 10-nucleotide gap region flanked by 5-nucleotide wings. Similarly, the motif "5-9-6" indicates a 9-nucleotide gap region flanked by 5-nucleotide wing on the 5' side and a 6-nucleotide wing on the 3' side. ISIS 29848 is a mixture of randomized oligomeric compounds, where each nucleotide can be A, T, C or G. For each compound listed in Table 2, the internucleoside (backbone) linkages are phosphorothioate throughout the oligonucleotide. Unmodified cytosines are indicated by ""C" in the nucleotide sequence; all other cytosines are 5-methylcytosines.

TABLE 2

Control oligonucleotides for cell line testing, oligomeric compound screening and phenotypic assays

| ISIS # | Target Name | Species of Target | Sequence (5' to 3') | Motif | SEQ ID NO |
|---|---|---|---|---|---|
| 113131 | CD86 | Human | CGTGTGTCTGTGCTAGTCCC | 5-10-5 | 6 |
| 289865 | forkhead box O1A (rhabdomyosarcoma) | Human | GGCAACGTGAACAGGTCCAA | 5-10-5 | 7 |
| 25237 | integrin beta 3 | Human | GCCCATTGCTGGACATGC | 4-10-4 | 8 |
| 196103 | integrin beta 3 | Human | AGCCCATTGCTGGACATGCA | 5-10-5 | 9 |
| 148715 | Jagged 2 | Human; Mouse; Rat | TTGTCCCAGTCCCAGGCCTC | 5-10-5 | 10 |
| 18076 | Jun N-Terminal Kinase-1 | Human | CTTTC"CGTTGGA"C"CCCTGGG | 5-9-6 | 11 |
| 18078 | Jun N-Terminal Kinase-2 | Human | GTGCG"CG"CGAG"C"C"CGAAATC | 5-9-6 | 12 |
| 183881 | kinesin-like 1 | Human | ATCCAAGTGCTACTGTAGTA | 5-10-5 | 13 |
| 29848 | none | none | NNNNNNNNNNNNNNNNNNNN | 5-10-5 | 14 |
| 226844 | Notch (*Drosophila*) homolog 1 | Human; Mouse | GCCCTCCATGCTGGCACAGG | 5-10-5 | 15 |
| 105990 | Peroxisome proliferator-activated receptor gamma | Human | AGCAAAAGATCAATCCGTTA | 5-10-5 | 16 |
| 336806 | Raf kinase C | Human | TACAGAAGGCTGGGCCTTGA | 5-10-5 | 17 |
| 15770 | Raf kinase C | Mouse; Murine sarcoma virus; Rat | ATGCATT"CTG"C"C"C"C"CAAGGA | 5-10-5 | 18 |
| 141923 | none | none | CCTTCCCTGAAGGTTCCTCC | 5-10-5 | 146 |

The concentration of oligonucleotide used varies from cell line to cell line. To determine the optimal oligonucleotide concentration for a particular cell line, the cells are treated with a positive control oligonucleotide at a range of concentrations. Positive controls are shown in Table 2. For human and non-human primate cells, the positive control oligonucleotide is selected from either ISIS 336806 or ISIS 18078. For mouse or rat cells the positive control oligonucleotide is ISIS 15770. The concentration of positive control oligonucleotide that results in 80% inhibition of the target mRNA, for example, human Raf kinase C for ISIS 336806, is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 1 µM to 40 µM when the antisense oligonucleotide is transfected by electroporation.

EXAMPLE 2

Real-Time Quantitative PCR Analysis of HBXIP mRNA Levels

Quantitation of HBXIP mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus MgCl$_2$, 6.6 mM MgCl$_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 µL of RiboGreen working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

Presented in Table 3 are primers and probes used to measure GAPDH expression in the cell types described herein. The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

TABLE 3

GAPDH primers and probes for use in real-time PCR

| Target Name | Species | Sequence Description | Sequence (5' to 3') | SEQ ID NO |
|---|---|---|---|---|
| GAPDH | Human | Forward Primer | CAACGGATTTGGTCGTATTGG | 19 |
| GAPDH | Human | Reverse Primer | GGCAACAATATCCACTTTACCAGAGT | 20 |
| GAPDH | Human | Probe | CGCCTGGTCACCAGGGCTGCT | 21 |
| GAPDH | Human | Forward Primer | GAAGGTGAAGGTCGGAGTC | 22 |
| GAPDH | Human | Reverse Primer | GAAGATGGTGATGGGATTTC | 23 |
| GAPDH | Human | Probe | CAAGCTTCCCGTTCTCAGCC | 24 |
| GAPDH | Human | Forward Primer | GAAGGTGAAGGTCGGAGTC | 22 |
| GAPDH | Human | Reverse Primer | GAAGATGGTGATGGGATTTC | 23 |
| GAPDH | Human | Probe | TGGAATCATATTGGAACATG | 25 |
| GAPDH | Mouse | Forward Primer | GGCAAATTCAACGGCACAGT | 26 |
| GAPDH | Mouse | Reverse Primer | GGGTCTCGCTCCTGGAAGAT | 27 |
| GAPDH | Mouse | Probe | AAGGCCGAGAATGGGAAGCTTGT-CATC | 28 |
| GAPDH | Rat | Forward Primer | TGTTCTAGAGACAGCCGCATCTT | 29 |
| GAPDH | Rat | Reverse Primer | CACCGACCTTCACCATCTTGT | 30 |
| GAPDH | Rat | Probe | TTGTGCAGTGCCAGCCTCGTCTCA | 31 |

Probes and primers for use in real-time PCR were designed to hybridize to target-specific sequences. The primers and probes and the HBXIP nucleic acid sequences to which they hybridize are presented in Table 4. The target-specific PCR probes have FAM covalently linked to the 5' end and TAMRA or MGB covalently linked to the 3' end, where FAM is the fluorescent dye and TAMRA or MGB is the quencher dye.

TABLE 4

HBXIP-specific primers and probes for use in real-time PCR

| Species | Target SEQ ID NO | Sequence Description | Sequence (5' to 3') | SEQ ID NO |
|---|---|---|---|---|
| Human | 1 | Forward Primer | TGGGAACATTATGATCCAGAAACA | 32 |
| Human | 1 | Reverse Primer | TGAGCATCAAGAGGCCATTTT | 33 |
| Human | 1 | Probe | TGGCATCACGGTGGCAGTGCA | 34 |
| Mouse | 5 | Forward Primer | TCTGGGCTGCCGTGGTA | 35 |
| Mouse | 5 | Reverse Primer | GCTGCCTGCTGGGCTAGA | 36 |
| Mouse | 5 | Probe | CGGATGAGCACGCTGGAGTCAT | 37 |

EXAMPLE 3

Treatment of Cultured Cells with Oligomeric Compounds

Oligomeric compounds targeted to HBXIP nucleic acids presented in Table 1 were tested for their effects on HBXIP expression in cultured cells. Table 5 shows the experimental conditions, including cell type, transfection method, dose of oligonucleotide and control SEQ ID NO used to evaluate the inhibition of gene expression by the oligomeric compounds of the invention. The control oligonucleotide was chosen from the group presented in Table 2, and in these experiments was used as a negative control. Each cell type was treated with the indicated dose of oligonucleotide as described by other examples herein. The oligomeric compounds and the data describing the degree to which they inhibit gene expression are shown in Table 6.

TABLE 5

Treatment conditions of cultured cells with oligomeric compounds

| Target Name | Cell Type | Transfection Method | Dose of Oligonucleotide (nM) | Control SEQ ID NO |
|---|---|---|---|---|
| HBXIP | b.END | Lipofectin | 10 | 12 |
| HBXIP | T-24 | Lipofectin | 100 | 12 |

EXAMPLE 4

Antisense Inhibition of HBXIP by Oligomeric Compounds

A series of oligomeric compounds was designed to target different regions of each target sequence, using published sequences cited in Table 1. The compounds are shown in Table 6. All compounds in Table 6 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein. Data are averages from experiments in which cultured cells were treated with the disclosed oligomeric compounds. Shown in Table 6 is the SEQ ID NO of the sequence to which each oligomeric compound is targeted. The inhibition data presented in Table 6 were obtained in a cell line derived from the same species as the indicated target sequence. The species of each target sequence is shown in Table 1.

A reduction in expression is expressed as percent inhibition in Table 6. If the target expression level of oligomeric compound-treated cell was higher than control, percent inhibition is expressed as zero inhibition.

TABLE 6

Inhibition of HBXIP mRNA levels by chimeric oligonucleotides having 2'-MOE wings and deoxy gap

| ISIS # | Target SEQ ID NO | Target Site | Sequence (5' -3') | % Inhibition | SEQ ID NO |
|---|---|---|---|---|---|
| 212391 | 1 | 266 | GGCTCAGAACCCAGCGGCAC | 80 | 38 |
| 212439 | 1 | 270 | CTCCGGCTCAGAACCCAGCG | 84 | 39 |
| 212403 | 1 | 272 | CACTCCGGCTCAGAACCCAG | 44 | 40 |

TABLE 6-continued

Inhibition of HBXIP mRNA levels by chimeric oligonucleotides having 2'-MOE wings and deoxy gap

| ISIS # | Target SEQ ID NO | Target Site | Sequence (5'-3') | % Inhibition | SEQ ID NO |
|---|---|---|---|---|---|
| 212349 | 1 | 304 | GCTCCAAGGTCGCCTCCATC | 55 | 41 |
| 212357 | 1 | 310 | AGTGCTGCTCCAAGGTCGCC | 67 | 42 |
| 212394 | 1 | 315 | TTCCAAGTGCTGCTCCAAGG | 63 | 43 |
| 212406 | 1 | 316 | CTTCCAAGTGCTGCTCCAAG | 64 | 44 |
| 212365 | 1 | 328 | TCTTCATTGTGTCTTCCAAG | 37 | 45 |
| 212369 | I | 365 | TGTGAATCTGTGCACAGGAC | 82 | 46 |
| 212431 | 1 | 376 | GATTAAGTCCTTGTGAATCT | 17 | 47 |
| 212359 | 1 | 391 | TCCCGCGGCAACCCAGATTA | 72 | 48 |
| 212378 | 1 | 412 | CAGCATGCTCATCTGACAGG | 82 | 49 |
| 212437 | 1 | 416 | ACTCCAGCATGCTCATCTGA | 78 | 50 |
| 212381 | 1 | 442 | CTGCTTGCTGGGCTAGAACA | 45 | 51 |
| 212397 | 1 | 491 | GATTCTAGACACACCACAGG | 33 | 52 |
| 212371 | 1 | 503 | TTCCCATTATCTGATTCTAG | 59 | 53 |
| 212376 | 1 | 517 | TCTGGATCATAATGTTCCCA | 84 | 54 |
| 212385 | 1 | 520 | GTTTCTGGATCATAATGTTC | 71 | 55 |
| 212373 | 1 | 528 | GCCATCGTGTTTCTGGATCA | 99 | 56 |
| 212412 | 1 | 538 | CCACCGTGATGCCATCGTGT | 98 | 57 |
| 212387 | 1 | 559 | AAGAGGCCATTTTGTGCACT | 53 | 58 |
| 212351 | 1 | 569 | TATGAGCATCAAGAGGCCAT | 71 | 59 |
| 212421 | 1 | 603 | ATCCAGTTCCTATGACAGGC | 91 | 60 |
| 212409 | 1 | 605 | GGATCCAGTTCCTATGACAG | 81 | 61 |
| 212424 | 1 | 606 | AGGATCCAGTTCCTATGACA | 77 | 62 |
| 212435 | 1 | 612 | ATAGGTAGGATCCAGTTCCT | 83 | 63 |
| 212400 | 1 | 635 | AGTAGTTCTATAAGGTAATT | 67 | 64 |
| 212418 | 1 | 654 | GCCTAACTACTGGAACTTTA | 88 | 65 |
| 212367 | 1 | 786 | AAAGTGACCTGGACCTGCTG | 89 | 66 |
| 212361 | 1 | 787 | CAAAGTGACCTGGACCTGCT | 89 | 67 |
| 212353 | 1 | 810 | TGAATACAGCAAAATTCTAT | 34 | 68 |
| 212433 | 1 | 814 | TTATTGAATACAGCAAAATT | 0 | 69 |
| 212363 | 1 | 819 | CAGATTTATTGAATACAGCA | 83 | 70 |
| 212355 | 1 | 830 | TTTCCTCCAAACAGATTTAT | 45 | 71 |
| 352092 | 3 | 275 | CCGTTTCCCAAACTTCTCAA | 68 | 72 |
| 352084 | 4 | 459 | CACTACTCACGTGTCCTCCA | 0 | 73 |
| 352085 | 4 | 1277 | AGACACTTACAGCCCAGATT | 25 | 74 |
| 352086 | 4 | 2692 | TGTCCCCCGAGTCTTTACTA | 46 | 75 |
| 352087 | 4 | 3372 | ATGTACTCACCCATTATCTG | 5 | 76 |

TABLE 6-continued

Inhibition of HBXIP mRNA levels by chimeric oligonucleotides having 2'-MOE wings and deoxy gap

| ISIS # | Target SEQ ID NO | Target Site | Sequence (5' -3') | % Inhibition | SEQ ID NO |
|---|---|---|---|---|---|
| 352088 | 4 | 3842 | CATTTTCTCTGCTACACTGG | 31 | 77 |
| 352089 | 4 | 4100 | GCTCCTGGTTCTAATTTTAA | 57 | 78 |
| 352090 | 4 | 4132 | CAAGCACGTCTATTTGCTTA | 41 | 79 |
| 352091 | 4 | 4980 | CATAATGTTCCTGAAAAGCC | 0 | 80 |
| 352019 | 5 | 22 | AGTGATGGCTGGCTTTCGAT | 0 | 81 |
| 352020 | 5 | 47 | AAGGCATAGCTACTACCACA | 7 | 82 |
| 352021 | 5 | 51 | CGAAAAGGCATAGCTACTAC | 11 | 83 |
| 352022 | 5 | 59 | GCTCTTTACGAAAAGGCATA | 0 | 84 |
| 352023 | 5 | 130 | GTGACTTGACCGAGGCGGGC | 9 | 85 |
| 352024 | 5 | 143 | AAACCTCGATCACGTGACTT | 22 | 86 |
| 352025 | 5 | 167 | GCAAACACTTCCTCCTTCA | 35 | 87 |
| 352026 | 5 | 221 | GCTCCAAAGTCGCCTCCATC | 18 | 88 |
| 352027 | 5 | 226 | ATGCTGCTCCAAAGTCGCCT | 47 | 89 |
| 352028 | 5 | 231 | TCCAAATGCTGCTCCAAAGT | 22 | 90 |
| 352029 | 5 | 236 | TGTCCTCCAAATGCTGCTCC | 2 | 91 |
| 352030 | 5 | 241 | CATTGTGTCCTCCAAATGCT | 17 | 92 |
| 352031 | 5 | 246 | TTCTTCATTGTGTCCTCCAA | 31 | 93 |
| 352032 | 5 | 251 | ATGGATTCTTCATTGTGTCC | 16 | 94 |
| 352033 | 5 | 256 | AATGGATGGATTCTTCATTG | 41 | 95 |
| 352034 | 5 | 261 | CCAACAATGGATGGATTCTT | 45 | 96 |
| 352035 | 5 | 266 | GGACTCCAACAATGGATGGA | 80 | 97 |
| 352036 | 5 | 271 | GCATAGGACTCCAACAATGG | 80 | 98 |
| 352037 | 5 | 276 | TCTGTGCATAGGACTCCAAC | 54 | 99 |
| 352038 | 5 | 281 | GTGAATCTGTGCATAGGACT | 69 | 100 |
| 352039 | 5 | 288 | AGTCCTTGTGAATCTGTGCA | 81 | 101 |
| 212431 | 5 | 293 | GATTAAGTCCTTGTGAATCT | 24 | 47 |
| 352040 | 5 | 301 | GCAGCCCAGATTAAGTCCTT | 54 | 102 |
| 352041 | 5 | 306 | CCACGGCAGCCCAGATTAAG | 46 | 103 |
| 352042 | 5 | 311 | GGGTACCACGGCAGCCCAGA | 65 | 104 |
| 352043 | 5 | 316 | CGACAGGGTACCACGGCAGC | 59 | 105 |
| 352044 | 5 | 321 | TCATCCGACAGGGTACCACG | 37 | 106 |
| 352045 | 5 | 354 | TGCTGGGCTAGAACAGATAT | 26 | 107 |
| 352046 | 5 | 400 | ACATACCACAGGGATGTCGG | 31 | 108 |
| 352047 | 5 | 421 | GTTCCCATTATCTGATTCTA | 36 | 109 |
| 352048 | 5 | 426 | ATAATGTTCCCATTATCTGA | 23 | 110 |
| 212376 | 5 | 434 | TCTGGATCATAATGTTCCCA | 68 | 54 |
| 212385 | 5 | 437 | GTTTCTGGATCATAATGTTC | 61 | 55 |

TABLE 6-continued

Inhibition of HBXIP mRNA levels by chimeric oligonucleotides having 2'-MOE wings and deoxy gap

| ISIS # | Target SEQ ID NO | Target Site | Sequence (5'-3') | % Inhibition | SEQ ID NO |
|---|---|---|---|---|---|
| 352049 | 5 | 442 | ATCGTGTTTCTGGATCATAA | 62 | 111 |
| 212373 | 5 | 445 | GCCATCGTGTTTCTGGATCA | 89 | 56 |
| 352050 | 5 | 447 | ATGCCATCGTGTTTCTGGAT | 85 | 112 |
| 352051 | 5 | 452 | CTGTGATGCCATCGTGTTTC | 53 | 113 |
| 352052 | 5 | 457 | AGCCACTGTGATGCCATCGT | 74 | 114 |
| 352053 | 5 | 462 | TGCACAGCCACTGTGATGCC | 73 | 115 |
| 352054 | 5 | 467 | TTTTGTGCACAGCCACTGTG | 30 | 116 |
| 352055 | 5 | 472 | GGCCATTTTGTGCACAGCCA | 85 | 117 |
| 352056 | 5 | 477 | CAAGAGGCCATTTTGTGCAC | 52 | 118 |
| 352057 | 5 | 482 | GATGTCAAGAGGCCATTTTG | 19 | 119 |
| 352058 | 5 | 487 | CATCAGATGTCAAGAGGCCA | 58 | 120 |
| 352059 | 5 | 498 | TGGAGAGCTGACATCAGATG | 32 | 121 |
| 352060 | 5 | 503 | GCCACTGGAGAGCTGACATC | 56 | 122 |
| 352061 | 5 | 527 | GGCATGACTGAATCCCGGTG | 96 | 123 |
| 352062 | 5 | 532 | AGACAGGCATGACTGAATCC | 46 | 124 |
| 352063 | 5 | 543 | CAAATGAGCTGAGACAGGCA | 56 | 125 |
| 352064 | 5 | 560 | GAACTTTAATAGTTTTACAA | 6 | 126 |
| 352065 | 5 | 567 | ATTTCTGGAACTTTAATAGT | 31 | 127 |
| 352066 | 5 | 572 | GGCCTATTTCTGGAACTTTA | 83 | 128 |
| 352067 | 5 | 591 | CATTGGACATTAACTGAATG | 26 | 129 |
| 352068 | 5 | 594 | CCACATTGGACATTAACTGA | 51 | 130 |
| 352069 | 5 | 611 | CATATAAATAAGGGAGTCCA | 20 | 131 |
| 352070 | 5 | 615 | CTGTCATATAAATAAGGGAG | 39 | 132 |
| 352071 | 5 | 643 | CCTCTCTAACTGATGTCTTG | 58 | 133 |
| 352072 | 5 | 647 | TGCTCCTCTCTAACTGATGT | 79 | 134 |
| 352073 | 5 | 660 | AAGCCCAAACAATTGCTCCT | 64 | 135 |
| 352074 | 5 | 673 | AGCAGAGTGACAAAAGCCCA | 66 | 136 |
| 352075 | 5 | 681 | CACCAAAGAGCAGAGTGACA | 55 | 137 |
| 352076 | 5 | 742 | TCAGCCTGGGCTACATAGTT | 66 | 138 |
| 352077 | 5 | 747 | TGAAGTCAGCCTGGGCTACA | 71 | 139 |
| 352078 | 5 | 767 | AAGCAGGAAGACCATACATT | 57 | 140 |
| 352079 | 5 | 795 | TGCTTTAATTCCAGGATGTA | 81 | 141 |
| 352080 | 5 | 802 | TGACAAATGCTTTAATTCCA | 10 | 142 |
| 352081 | 5 | 822 | CAAAGTGACCTAAACCTTAG | 25 | 143 |
| 352082 | 5 | 830 | TCTATATACAAAGTGACCTA | 44 | 144 |
| 352083 | 5 | 854 | CAGGTTTATTGGCCATAATG | 63 | 145 |

The results demonstrate that most of the antisense compounds targeting HBXIP resulted in inhibition of HBXIP mRNA levels. Treatment of cells with antisense compounds represented by SEQ ID NOs: 38-68, 70-72, 74, 75, 77-79, 86, 87, 89, 90, 93, 95-118, 120-125, 127-141 and 143-145 resulted in at least 20% inhibition of HBXIP mRNA; SEQ ID NOs: 38-44, 46, 48-51, 53-67, 70-72, 75, 78, 79, 89, 95-105, 111-115, 117, 118, 120, 122-125, 128, 130, 133-141, 144 and 145 resulted in at least 40% inhibition of HBXIP mRNA; SEQ ID NOs: 38, 39, 42-44, 46, 48-50, 54-57, 59-67, 70, 72, 97, 98, 100, 101, 104, 111, 112, 114, 115, 117, 123, 128, 134-136, 138, 139, 141 and 145 resulted in at least 60% inhibition of HBXIP mRNA; SEQ ID NOs: 38, 39, 46, 48-50, 54-57, 59-63, 65-67, 70, 97, 98, 101, 112, 114, 115, 117, 123, 128, 134, 139 and 141 resulted in at least 70% inhibition of HBXIP mRNA; SEQ ID NOs: 38, 39, 46, 49, 54, 56, 57, 60, 61, 63, 65-67, 70, 97, 98, 101, 112, 117, 123 and 128 resulted in at least 80% inhibition of HBXIP mRNA; and SEQ ID NOs: 56, 57, 60 and 123 resulted in at least 90% inhibition of HBXIP mRNA.

EXAMPLE 5

Dose-Dependent Inhibition of Mouse HBXIP Using Antisense Compounds

In accordance with the present invention, a set of mouse HBXIP antisense compounds was selected for a dose-response study in b.END cells. Using Lipofectin, cells were transfected with HBXIP antisense oligonucleotides ISIS 352061, ISIS 352073, ISIS 352050, ISIS 352055 or ISIS 352066, or control oligonucleotide ISIS 141923 at a concentration of 2.5, 5, 10 or 20 nM. The compounds were analyzed for their effect on HBXIP mRNA levels by quantitative real-time PCR as described in other examples herein. Data are averages from experiments in which cultured cells were treated with the disclosed oligomeric compounds. The results, shown in Table 7, are expressed as percent expression at each dose, relative to untreated control.

TABLE 7

Dose-dependent inhibition of HBXIP mRNA levels by antisense compounds

| ISIS # | 2.5 nM | 5.0 nM | 10 nM | 20 nM |
| --- | --- | --- | --- | --- |
| 352061 | 42 | 25 | 17 | 13 |
| 352073 | 54 | 43 | 24 | 15 |
| 352050 | 67 | 53 | 28 | 16 |
| 352055 | 69 | 36 | 28 | 12 |
| 352066 | 74 | 56 | 45 | 31 |
| 141923 | 92 | 90 | 82 | 83 |

The results demonstrate that each HBXIP antisense oligonucleotide significantly inhibited HBXIP mRNA expression and inhibition was dose-dependent.

EXAMPLE 6

Antisense Inhibition of HBXIP in HCC Cell Lines

In accordance with the present invention, HBXIP antisense compounds can be analyzed in HCC cell lines to identify compounds that inhibit HBXIP expression and/or enhance apoptosis. Such human cell lines include, but are not limited to, Hep3B, HepG2, Huh7, SNU449, SNU398, SNU423, HCCLM3 and 7721. Examples of mouse HCC cell lines included, but are not limited to, Hepa1c1c and MHT. Primary hepatocytes can also be used to identify effective antisense compounds. Cells are transfected with the antisense compounds of invention and levels of HBXIP are determined according to the methods described herein. The percentage of cells undergoing apoptosis can also be determined according to any one of the methods well known to those of skill in the art.

EXAMPLE 7

Antisense Inhibition of HBXIP in a Mouse Model of HCC

To identify HBXIP antisense compounds effective for the treatment of HCC, selected compounds can be tested in a mouse model of HCC. One such model is the SV40 transgenic HCC model (Taconic, Germantown, N.Y.) in which transgenic male mice express SV40 T-antigen in the liver, which leads to the spontaneous development of well-differentiated HCC. HCC mice are treated with one or more antisense compounds of the invention and levels of HBXIP in the liver are determined according to methods described herein and well known to those of skill in the art. HCC mice treated with antisense compounds can be further evaluated for tumor size, metastasis and survival.

SEQUENCE LISTING

```
<160> NUMBER OF SEQ ID NOS: 146

<210> SEQ ID NO 1
<211> LENGTH: 855
<212> TYPE: DNA
<213> ORGANISM: Homo sapiens

<400> SEQUENCE: 1
gaggcccggc tgcagacctc tcccgagagg ggaataatcc gtgccggccg gttccgccat      60
ggagccaggt gcaggtcacc tcgacggtca ccgcgcgggg agcccaagcc ttcgtcaggc     120
tctgtgcgac ggaagcgcag tgatgttttc cagtaaagaa cgcggacgtt gcaccgtgat     180
caattttgtc cctttggagg cgccgttacg gtccacgccc cgctcgcgtc aagtgactga     240
ggcctgtggt ggagaaggac gtgccgtgcc gctgggttct gagccggagt ggtcggtggg     300
```

```
tgggatggag gcgaccttgg agcagcactt ggaagacaca atgaagaatc cctccattgt    360
tggagtcctg tgcacagatt cacaaggact taatctgggt tgccgcggga ccctgtcaga    420
tgagcatgct ggagtgatat ctgttctagc ccagcaagca gctaagctaa cctctgaccc    480
cactgatatt cctgtggtgt gtctagaatc agataatggg aacattatga tccagaaaca    540
cgatggcatc acggtggcag tgcacaaaat ggcctcttga tgctcatatc tgttcttcag    600
cagcctgtca taggaactgg atcctaccta tgttaattac cttatagaac tactaaagtt    660
ccagtagtta ggccattcat ttaatgtgca ttaggcactt ttctgtttat ttaagagtca    720 attgcttttct aatgctctat ggaccgacta tcaagatatt agtaagaaag gatcatgttt    780
tgaagcagca ggtccaggtc actttgtata tagaattttg ctgtattcaa taaatctgtt    840
tggaggaaaa aaaaa                                                    855

<210> SEQ ID NO 2
<211> LENGTH: 7468
<212> TYPE: DNA
<213> ORGANISM: Homo sapiens

<400> SEQUENCE: 2
ttttaaaagt tattttcaag tagtcctacc cagtcttcct tacgagttag gactcaaatg     60
ccactctctt ccctaaact gtcctgagtc ccctcaccat aataagcacc aatgtcttcg     120
ttaaaatccc gacactgcca acactcagct aggggttga accttgctcc atctcgtcct     180
ttagtctctg tgtgcgtctt tcccctaca agcctactga ccccctccaa gaggtcccgt     240
gtcttccccg tacttgcccc acaggctaga tcagaccctg tctgacccct gggttattgt     300
aaaacttaag atctgtcccc taggtctcgg agtcggttga actagggtcc aaaggttaaa     360
aaacactgac acaaaatgcc aggccacgaa ctgaagcact gaggcccggc tgcagacctc     420
tcccgagagg ggaataatcc gtgccggccg gttcgccat ggagccaggt gcaggtcacc     480
tcgacggtca ccgcgcgggg agcccaagcc ttcgtcaggc tctgtgcgac ggaagcgcag     540
tgatgttttc cagtaaagaa cgcggacgtt gcaccgtgat caattttgtc cctttggagg     600
cgccgttacg gtccacgccc cgctcgcgtc aagtgactga ggcctgtggt ggagaaggac     660
gtgccgtgcc gctgggttct gagccggagt ggtcggtggg tgggatggag cgaccttgg     720 agcagcactt ggaagacacg tgagtagtgc gcgcctcttc ggcctgtcct gaggtcgcgg     780
cggaggaact tgagcggaac gaaaggcgcg agctgcgagt accggccagg gcgtctcggg     840
gacgtcgcgc gaccccgggg acacgggatg aggggctaa actctaccca aggccgcagg     900
gcggggcggg tgaccggaa ttaaaatcct gccgggcacc gcacattccc tcttgagcga     960
gtctcccggg cccaggccac gggccaaaac tgcctatctc gttgttgaaa tcgtctttac    1020
ggtcagggtg gttctgcgga agtttttagaa aacgggttga cttttgggaa gattgtgcca    1080
gttgtgcagt gtcgagccct gcagtgtaaa caaacacgta tctcctgtgt gtaacctatc    1140
agttacttgg tgcttaagta gataaaaatc attctttaaa tttttcgaac aagcagtatc    1200
tatgtaaaat tcaaaactgg aaaagtgtaa agggtacaga gagacacctg cctcccaccg    1260
atgtccctca gcttccactt accctccagg aggtaacttg agtttttcaa cagttgtttt    1320
aaatgagtta gtactaaaac atgcgttttt aacaagagtg aaaacatcct agatgttttt    1380
cacgcagtgt ttgtggccct ccagaactca gcagtactta gcacatttt ttctctcatc    1440 agagagaaac tggtttattt caattaatta actagaactt aaattttttg tgttcttttt    1500
ttgagacgga atttcgctcg tcttccaggc tggagtgcaa tggcgtgatc tcggctcact    1560
```

```
gcaacctccg cctcccaggt tcaagcgatt ctcttgcctc agcctcccga gtagctggga    1620
ttacagtcat gcgccaccac gcctggctaa ttttgtattt ttagtagaga cggggtttct    1680
ccatgttggt caggctggtc ttgaactccc gacctcaggt gatccgccca cctgggcctc    1740
ccaaagtgct gggattacag gcgtgagcaa ccgcgcccgg ccctagaact taatttttt     1800 cttagggtgt gacaatgaaa aaagattgag aaatattgat ttaaagcact taatgcctgg    1860
tacatagaac acctgtatgt ttgtacttat ttaaatcctt tttctcccat tatgtacttc    1920
aactctcttg tgttcctgga attagaatga agaatccctc cattgttgga gtcctgtgca    1980
cagattcaca aggacttaat ctgggttgta agtatctctc ataccaacta tttgatgaat    2040
tgcatagcat ctgatgttga cttggagcct agcgtgctat tattttctag cttttatttc    2100
ctgttacctt gccaggtctt tctgagtttg agagtagaga ttatctccaa ataacagtat    2160
cagaaaattg aaacttttca gttggtattt atgaaggaag atgttccttg cagtcctata    2220
acaataaata gttgtctcta ctaaaaataa tatttgaatc attttaaatt gagtctagaa    2280
aggacttcag ataataacag ctgttaacca tttattgaat gtatgccata tgctgagact    2340
gctaggctct aaatacatta tctttaattt tcacaacaac ccggcaaggt gggtggtgta    2400
caattttgaa gctcaactac actaaacaag aagtgaatag gcagtaaaat gggatttcag    2460
tgttggacat acctggtctc aatcccttgc tcttttcattt gttagtagtg tgaacgtgga    2520
ccaaaaaact acctttagg ccctcatttt cttcactggg ttgttatttg ataatggtaa    2580
taatcataga attatattta ttgagctgtt atgtgccaag caccattgta agtgctttac    2640
atatactctt ttattcctca taacaaccca gtgaggtaga aaagaaatt gagggaccag    2700 gtgcagtgtc tcacgcctgt aatcccagca cttgggaga ccaaggtggg cagatcactt    2760
gagcccagga gttcaagacc agcctgtgca acacagtgag acccccatc tctattttta    2820 caataaacat atatatatgt ttttaaaaatt taaaaaaaga ggccggatgc ggtggctcac    2880
acctgtgatc ccagcacttt gggaggcgga ggcgggtgga tcacctgagg tcaggagttc    2940
gagactagcc tggccaacat ggtgaaacca catctctact aaaaatgcaa aaaaaaatta    3000
gccaggcatg gtagcaggtg ctagtaatcc cagctactcg ggaggctgag gcaggagaat    3060
cgcttgaacc tgggaggcag aggttgcagt aagccgagat tgcaccattg cactccagcc    3120
tggatgacaa gagcgagact ctgtctcaaa aataaaaa agaaactgag acacagaggt    3180
taaataactt gcctgaggtc atgcagctag taagtcgtta agctaggatt tttgtctggc    3240
cctgaggcct cttaatcact tttttttttt tttttttgag acgaaatctt gctctgtcgc    3300
ccaggctaga gtgcagtggc acgatcttgg ctcactgcaa cctccatttc ccaggttcag    3360
gcaattctcc tgcctcagcc tcctgagtag ctgggattac aggcgcctgc caccacgccc    3420
agataatttt tgtattttta gtagatacag gtttcacta tgttggccag gctggtctcg    3480
aactccttat ctcaggtgat ccaccacct ccgcctccca aagtgcggga ttacaggaat    3540
gagccactac acccggccta atcacgatat tttaaggtta tataatatgt ataaaatgct    3600
tacatagaac tgagacataa tacttaataa atggtagcaa ttacacatga ggaaataagt    3660
ttggaaaggt aaataagtaa agcattcagt taattagtga caactagtaa acccaagact    3720
tgttgctcct aatgcaggaa tgtttaaagc tctgaatttt tgctggaagg gtaactgaaa    3780
gaggtaatcg gtgtaactca gttatgttta acatgcagat cagtcatttg ggagaaaaag    3840
ggtaaatttt tggaagcatt tgctaggctt actaatggaa agactgaaat tcaggtatgg    3900
aaatctaaaa ctaaatgagt tccttcaaga aaccttcaag gctcaaacgt cggcatcgga    3960
```

```
tctggtcaaa atgttttgta tagtaatagt acatccaaat gctctgccat agtggcatgt    4020
ctattacctg atttggtttc aggtacagtt aactttgtgt tgcctttata tacagaaata    4080
tattgtaaag tacacttagt aattaattt cgtacctaga atttataggt acttttgtac    4140
ccgagattta gttactataa tatatacaga ctaatacaga cattaataaa aagacaattc    4200
tgtagacatt ttaaaacagc cagctagctt attttagcag aaatactcta tgagcaatca    4260
ggtgacatat atcatctcta ttttccaggc cgcgggaccc tgtcagatga gcatgctgga    4320
gtgatatctg ttctagccca gcaagcagct aagctaacct ctgacccac tgatattcct     4380 gtggtgtgtc tagaatcaga taatgggtga gtagatttca gcagatcctt tccttttgt     4440 tcagaaaaat tcctggtaaa attggcgggg gccggccctg tgttcatcag tgattcctta    4500
ttcagactac tttgggaaaa gttcttaatc tttgaatca caggaacaga caagttgatc     4560
cctaaagcta atgtgctctc aggccacaat gctatttaaa tgaagaataa gaattggcag    4620
aagctatcag tttaccaaca aaagaaagt aacaaatagc acaaggaaa actaatcaga      4680 gaataaaaat tactttttt tttttctt tgaggcagg gtgttgctct ggcaccaggc       4740
tggagtacag tggtgtgatc atgggtcact gtgacttcaa ccccaccggg ctcaagcgat    4800
tcacccaact cagcctcccg agttgtagct gagactacag gtgtacacta ccacacccag    4860 ctaattttg tattttttg tagagatgag gtttcaccat gttcccagg ctggtctcga      4920 actcctgggc tccagtaatt tgcccgcctc agcctcccaa agtgctggga ttacaggaat    4980
gagtcactgc acccagccaa aaattacttc taaagcaata aaattactaa agatattcca    5040
agtgatggtc ctcagaataa tatgtgaaaa aaagtatata tatacaactg ctactatcac    5100
agccttgtaa aaagaaaaaa catacagtca tgcattgctt aacaatgggg atatgttctg    5160
agaaatgtgt caggcagttt tgttgtatga acatcataga gtgtacttaa acctaggtgg    5220
tacaccctat tacacaccta ggctgtattg ctcttagact acaaagattt gtagcctaaa    5280
taatgtaggc agttataaca gtggtattta tgtatctaaa cgtagagaag atacagtaaa    5340
agtatggtat agggaaattt tttaaaaggt atatctgaat agggcactta ccataatgga    5400
gcttacaaca ctggaagttg ctctgagtga gtcaataaaa ctttttgact ttataataac    5460
acttaaaaca gttgtacagc tgtacaaaaa ttctttttt aaactttttt acttttaga     5520 cttttttgtt aaaagcaaag aagaaacaca cattagccta ggcctgcaca gggtcaggat    5580
catcaatatc actggcttct atctccacat cttctcccac tggaaggtca tccagggcag    5640
taacatgcat ggagttgtca tctcctgtaa tgatgatacc ttctggaata cctcctaaag    5700
gacctgtctg aggctgtttt atagttaacc ttgtcttaat aagtaggagt agtatactct    5760
aaaataatga taaaaagtag gcccggcatg gtggctcaca cttgtaatcc cagcactttg    5820
ggaggccaag gcgggcagat cacttgaggt aaggagtgtg agacagccta accaacatgg    5880
tgaaaccctg tctctactaa aaatacaaaa attaggcatg gtggcaggca cctgtaatcc    5940
tagctactca ggaggctgag gcaggagaat tgcttgaacc cgggaggcag aggttgcagt    6000
gagctgagat cacgccactg ccctccagcc tgggcaacag agcaagactc cgtctcaaaa    6060
aaaagaaaaa aagtatagta aatacataaa ccatagcata gtcatttatt attatcaagc    6120
gttacgtact gtacataatt gtatgtgcta tactttttat gactggcagc acaatttgtt    6180
tacaccagca ttaccacaaa catgtgagta gtgtgttgtg ctatgtgatg ctgggacggt    6240
taaaaggtca ctaggcaata ggaattttc agttccatta taatcttacg ggaccaccat    6300
catatgtagg gtccactgtt gactgaagca ttgttatgca gcacatgact gtatcatata    6360
```

```
catgcaaaga aaacaaagac cagtaaagcc ttttttttgt agttccagct actgaggtgg    6420
ctgaagcagg attgcttgag cccaggagtt tgaggccagc ttgggcaaca tagcaagaca    6480
gtgcctaaaa aaccgaaaca agaaccagg gaaatattaa cagtggttgt ctgtgtgtag     6540
taggattaag gattcatttc gtgttcacat gctatatgtt tatgtatttc ccaaatgttt    6600
tgttatgttt aaatattgct tttatacgta gaaacaatta cattatttta aatattgtat    6660
cctaaagcaa acaacatctt taatcttgca gtgaagtccc actgattacg ttttactgaa    6720
tattttcttc ctgcatttca ggaacattat gatccagaaa cacgatgcca tcacggtggc    6780
agtgcacaaa atggcctctt gatgctcata tctgttcttc agcagcctgt cataggaact    6840
ggatcctacc tatgttaatt accttataga actactaaag ttccagtagt taggccattc    6900
atttaatgtg cattaggcac ttttctgttt atttaagagt caattgcttt ctaatgctct    6960
atggaccgac tatcaagata ttagtaagaa aggatcatgt tttgaagcag caggtccagg    7020
tcactttgta tatagaattt tgctgtattc aataaatctg tttggaggaa aatggatctt    7080
ttctagattc tttaaactta accaaatgtt ccttttgttc agttatcaaa ctgtaatttt    7140
tttaaaaggt ctttgttcta aattacttttt gtttaagaag cttcctgaaa tacctacatt   7200
ctcacaggta tgtccatgga tcccacccct gtgcagtcag aaatctacat gtaacttttg    7260 accctcagt agcctactga cttaaacagt aacacgagtt ttctatgttt tacgttttcg      7320
ttttttgttt tgtttttgttt tgtttttttc agtagacaga gtcctgctct gtcgccaggc   7380
tggagtgcag tggtgcgatc tcagctcact gcaagctccg cctcctgggt tcaagcgatt    7440
ctcctgcctc agcctccaga gtagctgg                                         7468

<210> SEQ ID NO 3
<211> LENGTH: 422
<212> TYPE: DNA
<213> ORGANISM: Mus musculus

<400> SEQUENCE: 3
gagtgttttg ctgcggggtc ctggcctggg gcggacagcc tgcgggatgg aggcgacttt     60
ggagcagcat ttggaggaca cgtgagtagt gcgtgcggcc ggtcctgggc tccggacagg    120
ggagctggaa tgggacagcg gcatggaccg cgagtgtctg cgcacagcgt ctggggcact    180
cggggcggcg agcgggtgac ttctgcctac ggccgagccg ctcgttactg ggtagtaaag    240
tttcgttagg cgtgttcgca caatcgagta gctcttgaga agtttgggaa acggattaag    300
tttggggaag gatgccccgg gtgtgctaaa tcgagccccc gcagtggcaa agcactttca    360
cgcacatctt cccgcgtcag tggcccgtca gttgctcagc gcctgtgaag taaatatatc    420
cg                                                                     422

<210> SEQ ID NO 4
<211> LENGTH: 6001
<212> TYPE: DNA
<213> ORGANISM: Mus musculus

<400> SEQUENCE: 4
cttgacctag ggtcagaaac tgagcactgt cttcttagcg attggcctat tgcatagatg      60
agaccatgcc agacctgctg gttactttaa aatttaaacc aggtctacgt ctggttagga    120
ctggaaattg cttgaaccaa atccaaaggt taaaaatcac taagtccaag tgctaggtca    180
ggaaaaggcc ctgaggcccg actacagatt gctttgaagg cccagcaccc caatcgaaa     240 gccagccatc actggtcctg tggtagtagc tatgcctttt cgtaaagagc gcggacgcgg    300
```

```
cgccgcgctg aatttcgtcc ctctggagac gccgtccagg cgcccgcctc ggtcaagtca    360
cgtgatcgag gtttgcggtg aaggaggaag tgttttgctg cggggtcctg gcctggggcg    420
gacagcctgc gggatggagg cgactttgga gcagcatttg gaggacacgt gagtagtgcg    480
tgcggccggt cctgggctcc ggacagggga gctggaatgg gacagcggca tggaccgcga    540
gtgtctgcgg aagcgtttgg ggcactcggg gcggcgagcg ggtgacttct gcctacggcc    600
gggccgctcg ttactgggta gtaaagtttc gttaggcgtg ttcgcagaat cgagtagctc    660
ttgagaagtt tgggaaacgg attaagtttg gggaaggatg ccccgggtgt gctaaatcga    720
gcccccgcag tgccaaagca cttcacgca catcttcccg cgtttgtggc ccgtcagttg    780
ctcagcgctt gtgaagtaaa tatatccgta aagttttca gctatctctg taaaatttaa    840
aattgggagg tgtaaagtgg cttacaagaa gacacctcct ccttgagctt cttaatcccc    900
tccaggagca attcccgtta ctgagattta acagttgtct tcaggagttg cagtcctaga    960
gcatgcttct ataccaagga cagagcccta agataactg ccttgtttgt gtctttgtga   1020
agcagaggtg cctgagaaaa tggttgggt tttgttttgt ttatttaaac aactcacagt   1080
ttgtcctctg aaaggggggcg aaaaaattta agggctgatt tgaagtgctt aatactcggt   1140
gcatagaaaa tctgttttac tacagtaatt tgaaatattt tcttcacatc atctggttca   1200
tctttcttgt gctcccaaaa ttagaatgaa gaatccatcc attgttggag tcctatgcac   1260
agattcacaa ggacttaatc tgggctgtaa gtgtctccta ccagcctccc tttgaagttc   1320
tgagagcctt aacttacact gctactattt tctagctttt attcctgtta cctttagggc   1380
atagagacta tctccaagta agagtagatg gttgaagcct ttcagttgca ttttaaaggc   1440
agaaatgttc ctcccagttc tacaactgtt cctactaaaa tggttttgaa taaattttaa   1500
gtggtctaga aaagggcttt agataaggac atctttactg aatgcattcc ctgtgcaggc   1560
acagtcaggc tacactattt ccttaattgc ctcaataacc ctgaaaatgg atgatgctgg   1620
ctgctagtcc agccactctc aacagtaagt tattgtcagt aaaaatgggg atttcctagt   1680
tagacacgtc tgacttcaac cccattctcc gatgctgtct gctagcaaca tgagtgccga   1740
acagaaggag cctcttgggg cttcagtttc ttcattgggt tattttattt catacataca   1800
ttatgtgtgt gttgtcttaa gacatttttt tttaaaaact tattctacgt ggccctggct   1860
gtcctggaac aaactttgta gaccatgctg gcctgtaact cacagagatc tgcctgcctc   1920
tatcccttga atgctgggaa caaaggtgtg catcaccatg cccagccagg cactattctt   1980
agtgttttca ttataaaacg tacataaccc cccttcctgc ccccccccc ccaccaaagc   2040
cctttatggt caagaaattt agcaagctta aaagtacctt gcccagggtc aaacacctaa   2100
tgaatggttg agataggatg ttttttaaagc tggctccaaa gcttaaaaca cccagtacag   2160
aaccaagatg tgtttgtgtg gtgttcaata aattgtagca attacagata aggaactaag   2220
tccagaaagg taaatagcta aagttaatta atgtcagaaa ctagtaaacc caagaatcct   2280
tataactgat gcaggttttt tagagctctg atcttttgct ggtatgatac ctgacaaaag   2340
taatatagtt atgtcttata caaaaagcag ccatttggaa caaaggtaaa ttttttgaa    2400
gcatttgcca agttactaat gaaaactctt taaatgcaaa tgtggaggaa aaaaaaaac    2460
taagtaaaac cttcaaggtg cgaagttgct atttccaata gatttccggg ctgcactttg   2520
gcctacggat ttttatgta gtaatagtca atccagaatt tctgccaggt tatattgtct   2580
actaccttag ttttaggtgt aagtaaaccc ctttatttca gggatctata ataagcttgg   2640
tggttacctt ttgtgcctag agcctgattt agttaataca agtcaaagta atagtaaaga   2700
```

```
ctcgggggac atttgaaagg agcccagcta gcttctgcta gcagaaatag ttgctcacag    2760
gtcttcacat atgctggcaa ggtgatctta caactggact tctgagtaat ggctgcttct    2820
ttgagattga gcataggaag agaaactcag atttcccata aggaattaat tagcatcaac    2880 aagccccta tccatactga atgcttttg tcactctcgc ctttgaattt cttggtttca     2940
```

```
gcaaggttcc tataaaatag ttactaccat cagatgactt gaattacagc ttccttatat    3000
gcttgagaag gtgtttagag atagtgaggg gaataactct gaaaactaca tgtcgtttac    3060
gactttgctg atttaagaac aattgccagg ctttctcact aatggactca gctgagtacc    3120
aggtgagaga gatcctttct tgtcagtact taacctaaag gcaaaaggc cgtgagcgga    3180 gtttcttttt cacaaataat tctggaggag atactaaact ataggtttat attaattttt    3240
agacacttct cactattctc taggccgtgg taccctgtcg gatgagcacg ctggagtcat    3300
atctgttcta gcccagcagg cagctaggct aacctctgac cccaccgaca tccctgtggt    3360
atgtttagaa tcagataatg ggtgagtaca taccagcaca ccctttctt tttgttctga    3420 aaaacttgat tgggctttcc cctgcattca gtggtagttc attagtcaat gcaccacaga    3480
gccattggac atccaggcct catgagaaca gaacttcatt aaaataagaa ctatcagttt    3540
gccactccaa taaggaaaa acagtaaaaa cacaaaaat gattagctgc atagaattcc     3600
ctaaagtaag gtcttaaaga tattcctaga taaagatctt tattcagatg ctaagtgata    3660 aaggaagaa acaaaactg tggggctgga gaaatgccag tgcttaagag ccacagtccc      3720
gaggatgaga gcttatatac tagtaccca gcacccacac aacaaacacc tgcaacctca     3780
gccctcagtc aggggcgagg gggtgggcag agatgggagg attgttggag ctggctgtcc    3840
tccagtgtag cagagaaaat gaggctcagg ctcaggata agaccacaca tcaaggata     3900 gttgcacagt aatagaggac acccagcacc ttcttctgac ctccgtgcct atacataggt    3960
gtgtgtacat gcacacacct gtatgtgcac acctgcacag atagagta tgtgaacctt     4020 taaaaatgca tactttggtc agtttggggc aagggaaaaa gaagatatta atatcgatat    4080
atgtataaat atatacaaat taaaattaga accaggagcc agcaagatgg ctaagcaaat    4140
agacgtgctt gctgccaagt ctgatgactg gaactccata cctggaaccc acatgactga    4200
ggagacaaac accctgacgt tgtcatgcaa gcagtggcac acatacagac ccccaaaata   4260
agtaacataa ataagaatta agagctgggg aggcggctca gtggttgaaa gcacatggca    4320
ctctcccaga ggacctgtgt cagttcccag cacccacatt tggaagttca caaccactta    4380
taactccaac tccagaggaa ccaacaccac tcgctggcct tctcaggcac cagtgtgtat    4440
aatgacacac acggacagac acatacatat atttttaaa aatctaatct aaaaattagg    4500
accaggaagg aggctaggct agtgatagca tgtgcaaggc tctagattct aactccaaca    4560
ataccaccaa aacctccagg aaaaaataaa aatcagaatc atgttgagta gtagggttaa    4620
ggattacttt ttaaaaattt ttttaatta aaaggattaa tttctttatg ttataattag    4680
atttgcccac aatcctcaac tgttcatgcc catctgtgct atttatttat tcatgtttct    4740
tagcggaaga cttggctctt ggtttgagaa tgtagtcccc tttctggggtg ggaagtatgg    4800 agaggctatg gcactagggg ttggtgacgg acacctgtca acagggactg ttcatatttg    4860
gttttgtatg agaatataga taaatatgct gtcatctaaa cataaatata tttaaactaa    4920 ataaattta tcttacactg agacacatgc attaagagtt tgctgaatat tttctttttg     4980
gcttttcagg aacattatga tccagaaaca cgatggcatc acagtggctg tgcacaaaat    5040
ggcctcttga catctgatgt cagctctcca gtggcctctc accgggattc agtcatgcct    5100
```

```
gtctcagctc atttgtaaaa ctattaaagt tccagaaata ggccattcag ttaatgtcca    5160
atgtggactc ccttatttat atgacagcca gttaccaaga catcagttag agaggagcaa    5220
ttgtttgggc ttttgtcact ctgctctttg gtgacagtca ctgtagtcca ggatcacagc    5280
ccatcatggc ctagaactat gtagcccagg ctgacttcaa atgtatggtc ttcctgcttt    5340
aaacacatac atcctggaat taaagcattt gtcactaagg tttaggtcac tttgtatata    5400
gaacttcatt atggccaata aacctgttct gaggaaagtt tggttcattt ctggtctttt    5460
aaaattccta cttaatgctc acttttcttt tttcagttat caaattgtgg gttttttggt    5520
tttttttttt tttttttttt ctctaaaaga tctctatccc aaactacttg tttctctttc    5580
ggtgtcttaa aatgtctgtg ttcttatgca agggaagatg gatcaaatat ttccctcaac    5640
ctaagtgaca aaggacatat cattgagtcc ttagtaagac cagaaactta tttctcatta    5700
taaaatagga taggtactcc tggttgttgt gtgtaaccaa agcctagggg ctagcatggt    5760
caccatcaga acttaagaac ttaactgaca gaaggcgtgt gtgctttgct ttgtttggtt    5820
ggttggttga tttttctgag acagggtttc tctgtgtagc cctggctgtc ctggaatttg    5880
gtagaccacg ttagcctcaa actcagagat ctgcctatct ctgcctccca agtgctagga    5940
ataaagatgt gcgccaccac tacccgacat ggacagacta cattttacc atcatccaga    6000 c                                                                    6001

<210> SEQ ID NO 5
<211> LENGTH: 881
<212> TYPE: DNA
<213> ORGANISM: Mus musculus

<400> SEQUENCE: 5
tttgaaggcc cagcaccccc aatcgaaagc cagccatcac tggtcctgtg gtagtagcta     60
tgccttttcg taaagagcgc ggacgcggcc ccgcgctgaa tttcgtccct ctggagacgc    120
cgtccaggcg cccgcctcgg tcaagtcacg tgatcgaggt ttgcggtgaa ggaggaagtg    180
ttttgctgcg gggtcctggc ctggggcgga cagcctgcgg gatggaggcg actttggagc    240
agcatttgga ggacacaatg aagaatccat ccattgttgg agtcctatgc acagattcac    300
aaggacttaa tctgggctgc cgtggtaccc tgtcggatga gcacgctgga gtcatatctg    360
ttctagccca gcaggcagct aggctaacct ctgaccccac cgacatccct gtggtatgtt    420
tagaatcaga taatgggaac attatgatcc agaaacacga tggcatcaca gtggctgtgc    480
acaaaatggc ctcttgacat ctgatgtcag ctctccagtg gcctctcacc gggattcagt    540
catgcctgtc tcagctcatt tgtaaaacta ttaaagttcc agaaataggc cattcagtta    600
atgtccaatg tggactccct tatttatatg acagccagtt accaagacat cagttagaga    660
ggagcaattg tttgggcttt tgtcactctg ctctttggtg acagtcactg tagtccagga    720
tcacagccca tcatggccta gaactatgta gcccaggctg acttcaaatg tatggtcttc    780
ctgctttaaa cacatacatc ctggaattaa agcatttgtc actaaggttt aggtcacttt    840
gtatatagaa cttcattatg gccaataaac ctgttctgag g                        881

<210> SEQ ID NO 6
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 6
```

```
cgtgtgtctg tgctagtccc                                              20

<210> SEQ ID NO 7
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 7
ggcaacgtga acaggtccaa                                              20

<210> SEQ ID NO 8
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 8
gcccattgct ggacatgc                                                18

<210> SEQ ID NO 9
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 9
agcccattgc tggacatgca                                              20

<210> SEQ ID NO 10
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 10
ttgtcccagt cccaggcctc                                              20

<210> SEQ ID NO 11
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 11
ctttccgttg gacccctggg                                              20

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
gtgcgcgcga gcccgaaatc                                              20

<210> SEQ ID NO 13
<211> LENGTH: 20
<212> TYPE: DNA
<213> ORGANISM: Artificial Sequence
```

```
<220> FEATURE:
<223> OTHER INFORMATION: Oligomeric Compound

<400> SEQUENCE: 13
atccaagtgc tactgtagta                                                    20

<210> SEQ ID NO 14
<211> LENGTH: 20
<212> TYPE: DNA
<213> ORGANISM: Artificial Sequence
<220> FEATURE:
<223> OTHER INFORMATION: Oligomeric Compound
<220> FEATURE:
<221> NAME/KEY: misc_feature
<222> LOCATION: 1-20
<223> OTHER INFORMATION: n is a, c, g, or t

<400> SEQUENCE: 14
nnnnnnnnnn nnnnnnnnnn                                                    20

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
gccctccatg ctggcacagg                                                    20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
agcaaaagat caatccgtta                                                    20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
tacagaaggc tgggccttga                                                    20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 18
atgcattctg cccccaagga                                                    20

<210> SEQ ID NO 19
<211> LENGTH: 21
<212> TYPE: DNA
<213> ORGANISM: Artificial Sequence
<220> FEATURE:
<223> OTHER INFORMATION: Forward Primer

<400> SEQUENCE: 19
```

-continued caacggattt ggtcgtattg g                                    21

<210> SEQ ID NO 20
<211> LENGTH: 26
<212> TYPE: DNA
<213> ORGANISM: Artificial Sequence
<220> FEATURE:
<223> OTHER INFORMATION: Reverse Primer

<400> SEQUENCE: 20
ggcaacaata tccactttac cagagt                               26

<210> SEQ ID NO 21
<211> LENGTH: 21
<212> TYPE: DNA
<213> ORGANISM: Artificial Sequence
<220> FEATURE:
<223> OTHER INFORMATION: Probe

<400> SEQUENCE: 21
cgcctggtca ccagggctgc t                                    21

<210> SEQ ID NO 22
<211> LENGTH: 19
<212> TYPE: DNA
<213> ORGANISM: Artificial Sequence
<220> FEATURE:
<223> OTHER INFORMATION: Forward Primer

<400> SEQUENCE: 22
gaaggtgaag gtcggagtc                                       19

<210> SEQ ID NO 23
<211> LENGTH: 20
<212> TYPE: DNA
<213> ORGANISM: Artificial Sequence
<220> FEATURE:
<223> OTHER INFORMATION: Reverse Primer

<400> SEQUENCE: 23
gaagatggtg atgggatttc                                      20

<210> SEQ ID NO 24
<211> LENGTH: 20
<212> TYPE: DNA
<213> ORGANISM: Artificial Sequence
<220> FEATURE:
<223> OTHER INFORMATION: Probe

<400> SEQUENCE: 24
caagcttccc gttctcagcc                                      20

<210> SEQ ID NO 25
<211> LENGTH: 20
<212> TYPE: DNA
<213> ORGANISM: Artificial Sequence
<220> FEATURE:
<223> OTHER INFORMATION: Probe

<400> SEQUENCE: 25
tggaatcata ttggaacatg                                      20

<210> SEQ ID NO 26
<211> LENGTH: 20
<212> TYPE: DNA
<213> ORGANISM: Artificial Sequence

```
<220> FEATURE:
<223> OTHER INFORMATION: Forward Primer

<400> SEQUENCE: 26
ggcaaattca acggcacagt                                              20

<210> SEQ ID NO 27
<211> LENGTH: 20
<212> TYPE: DNA
<213> ORGANISM: Artificial Sequence
<220> FEATURE:
<223> OTHER INFORMATION: Reverse Primer

<400> SEQUENCE: 27
gggtctcgct cctggaagat                                              20

<210> SEQ ID NO 28
<211> LENGTH: 27
<212> TYPE: DNA
<213> ORGANISM: Artificial Sequence
<220> FEATURE:
<223> OTHER INFORMATION: Probe

<400> SEQUENCE: 28
aaggccgaga atgggaagct tgtcatc                                      27

<210> SEQ ID NO 29
<211> LENGTH: 23
<212> TYPE: DNA
<213> ORGANISM: Artificial Sequence
<220> FEATURE:
<223> OTHER INFORMATION: Forward Primer

<400> SEQUENCE: 29
tgttctagag acagccgcat ctt                                          23

<210> SEQ ID NO 30
<211> LENGTH: 21
<212> TYPE: DNA
<213> ORGANISM: Artificial Sequence
<220> FEATURE:
<223> OTHER INFORMATION: Reverse Primer

<400> SEQUENCE: 30
caccgacctt caccatcttg t                                            21

<210> SEQ ID NO 31
<211> LENGTH: 24
<212> TYPE: DNA
<213> ORGANISM: Artificial Sequence
<220> FEATURE:
<223> OTHER INFORMATION: Probe

<400> SEQUENCE: 31
ttgtgcagtg ccagcctcgt ctca                                         24

<210> SEQ ID NO 32
<211> LENGTH: 24
<212> TYPE: DNA
<213> ORGANISM: Artificial Sequence
<220> FEATURE:
<223> OTHER INFORMATION: Forward Primer

<400> SEQUENCE: 32
tgggaacatt atgatccaga aaca                                         24
```

```
<210> SEQ ID NO 33
<211> LENGTH: 21
<212> TYPE: DNA
<213> ORGANISM: Artificial Sequence
<220> FEATURE:
<223> OTHER INFORMATION: Reverse Primer

<400> SEQUENCE: 33
tgagcatcaa gaggccattt t                                              21

<210> SEQ ID NO 34
<211> LENGTH: 21
<212> TYPE: DNA
<213> ORGANISM: Artificial Sequence
<220> FEATURE:
<223> OTHER INFORMATION: Probe

<400> SEQUENCE: 34
tggcatcacg gtggcagtgc a                                              21

<210> SEQ ID NO 35
<211> LENGTH: 17
<212> TYPE: DNA
<213> ORGANISM: Artificial Sequence
<220> FEATURE:
<223> OTHER INFORMATION: Forward Primer

<400> SEQUENCE: 35
tctgggctgc cgtggta                                                   17

<210> SEQ ID NO 36
<211> LENGTH: 18
<212> TYPE: DNA
<213> ORGANISM: Artificial Sequence
<220> FEATURE:
<223> OTHER INFORMATION: Reverse Primer

<400> SEQUENCE: 36
gctgcctgct gggctaga                                                  18

<210> SEQ ID NO 37
<211> LENGTH: 22
<212> TYPE: DNA
<213> ORGANISM: Artificial Sequence
<220> FEATURE:
<223> OTHER INFORMATION: Probe

<400> SEQUENCE: 37
cggatgagca cgctggagtc at                                             22

<210> SEQ ID NO 38
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 38
ggctcagaac ccagcggcac                                                20

<210> SEQ ID NO 39
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 39
```

```
ctccggctca gaacccagcg                                               20

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 40
cactccggct cagaacccag                                               20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
gctccaaggt cgcctccatc                                               20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
agtgctgctc caaggtcgcc                                               20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
ttccaagtgc tgctccaagg                                               20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
cttccaagtg ctgctccaag                                               20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
tcttcattgt gtcttccaag                                               20

<210> SEQ ID NO 46
<211> LENGTH: 20
<212> TYPE: DNA
<213> ORGANISM: Artificial Sequence
```

```
<220> FEATURE:
<223> OTHER INFORMATION: Oligomeric Compound

<400> SEQUENCE: 46
tgtgaatctg tgcacaggac                                               20

<210> SEQ ID NO 47
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 47
gattaagtcc ttgtgaatct                                               20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
tcccgcggca acccagatta                                               20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
cagcatgctc atctgacagg                                               20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
actccagcat gctcatctga                                               20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
ctgcttgctg ggctagaaca                                               20

<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52
gattctagac acaccacagg                                               20
```

```
<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
ttcccattat ctgattctag                                              20

<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
tctggatcat aatgttccca                                              20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
gtttctggat cataatgttc                                              20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
gccatcgtgt ttctggatca                                              20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
ccaccgtgat gccatcgtgt                                              20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
aagaggccat tttgtgcact                                              20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
```
tatgagcatc aagaggccat                                           20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 60
atccagttcc tatgacaggc                                           20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
ggatccagtt cctatgacag                                           20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
aggatccagt tcctatgaca                                           20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
ataggtagga tccagttcct                                           20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
agtagttcta taaggtaatt                                           20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
gcctaactac tggaacttta                                           20

<210> SEQ ID NO 66
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 66
aaagtgacct ggacctgctg                                               20

<210> SEQ ID NO 67
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 67
caaagtgacc tggacctgct                                               20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
tgaatacagc aaaattctat                                               20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
ttattgaata cagcaaaatt                                               20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
cagatttatt gaatacagca                                               20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
tttcctccaa acagatttat                                               20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
ccgtttccca aacttctcaa                                               20
```

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
cactactcac gtgtcctcca                                           20

<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
agacacttac agcccagatt                                           20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
tgtcccccga gtctttacta                                           20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
atgtactcac ccattatctg                                           20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
cattttctct gctacactgg                                           20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
gctcctggtt ctaattttaa                                           20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79

-continued caagcacgtc tatttgctta 20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 80
cataatgttc ctgaaaagcc 20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
agtgatggct ggctttcgat 20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
aaggcatagc tactaccaca 20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
cgaaaaggca tagctactac 20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
gctctttacg aaaaggcata 20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
gtgacttgac cgaggcgggc 20

<210> SEQ ID NO 86
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 86
aaacctcgat cacgtgactt                                               20

<210> SEQ ID NO 87
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 87
gcaaaacact tcctccttca                                               20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
gctccaaagt cgcctccatc                                               20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
atgctgctcc aaagtcgcct                                               20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
tccaaatgct gctccaaagt                                               20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
tgtcctccaa atgctgctcc                                               20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
cattgtgtcc tccaaatgct                                               20
```

```
<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
ttcttcattg tgtcctccaa                                               20

<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
atggattctt cattgtgtcc                                               20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
aatggatgga ttcttcattg                                               20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
ccaacaatgg atggattctt                                               20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
ggactccaac aatggatgga                                               20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
gcataggact ccaacaatgg                                               20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
```
tctgtgcata ggactccaac                                               20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 100
gtgaatctgt gcataggact                                               20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
agtccttgtg aatctgtgca                                               20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
gcagcccaga ttaagtcctt                                               20

<210> SEQ ID NO 103
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 103
ccacggcagc ccagattaag                                               20

<210> SEQ ID NO 104
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 104
gggtaccacg gcagcccaga                                               20

<210> SEQ ID NO 105
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 105
cgacagggta ccacggcagc                                               20

<210> SEQ ID NO 106
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 106
tcatccgaca gggtaccacg                                              20

<210> SEQ ID NO 107
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 107
tgctgggcta gaacagatat                                              20

<210> SEQ ID NO 108
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 108
acataccaca gggatgtcgg                                              20

<210> SEQ ID NO 109
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 109
gttcccatta tctgattcta                                              20

<210> SEQ ID NO 110
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 110
ataatgttcc cattatctga                                              20

<210> SEQ ID NO 111
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 111
atcgtgtttc tggatcataa                                              20

<210> SEQ ID NO 112
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 112
atgccatcgt gtttctggat                                              20
```

```
<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
ctgtgatgcc atcgtgtttc                                            20

<210> SEQ ID NO 114
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 114
agccactgtg atgccatcgt                                            20

<210> SEQ ID NO 115
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 115
tgcacagcca ctgtgatgcc                                            20

<210> SEQ ID NO 116
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 116
ttttgtgcac agccactgtg                                            20

<210> SEQ ID NO 117
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 117
ggccattttg tgcacagcca                                            20

<210> SEQ ID NO 118
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 118
caagaggcca ttttgtgcac                                            20

<210> SEQ ID NO 119
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 119
```

```
gatgtcaaga ggccattttg                                                20

<210> SEQ ID NO 120
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 120
catcagatgt caagaggcca                                                20

<210> SEQ ID NO 121
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 121
tggagagctg acatcagatg                                                20

<210> SEQ ID NO 122
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 122
gccactggag agctgacatc                                                20

<210> SEQ ID NO 123
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 123
ggcatgactg aatcccggtg                                                20

<210> SEQ ID NO 124
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 124
agacaggcat gactgaatcc                                                20

<210> SEQ ID NO 125
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 125
caaatgagct gagacaggca                                                20

<210> SEQ ID NO 126
<211> LENGTH: 20
<212> TYPE: DNA
<213> ORGANISM: Artificial Sequence
```

<220> FEATURE:
<223> OTHER INFORMATION: Oligomeric Compound

<400> SEQUENCE: 126
gaactttaat agttttacaa                                           20

<210> SEQ ID NO 127
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 127
atttctggaa ctttaatagt                                           20

<210> SEQ ID NO 128
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 128
ggcctatttc tggaacttta                                           20

<210> SEQ ID NO 129
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 129
cattggacat taactgaatg                                           20

<210> SEQ ID NO 130
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 130
ccacattgga cattaactga                                           20

<210> SEQ ID NO 131
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 131
catataaata agggagtcca                                           20

<210> SEQ ID NO 132
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 132
ctgtcatata aataagggag                                           20

```
<210> SEQ ID NO 133
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 133
cctctctaac tgatgtcttg                                               20

<210> SEQ ID NO 134
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 134
tgctcctctc taactgatgt                                               20

<210> SEQ ID NO 135
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 135
aagcccaaac aattgctcct                                               20

<210> SEQ ID NO 136
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 136
agcagagtga caaaagccca                                               20

<210> SEQ ID NO 137
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 137
caccaaagag cagagtgaca                                               20

<210> SEQ ID NO 138
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 138
tcagcctggg ctacatagtt                                               20

<210> SEQ ID NO 139
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 139
```
tgaagtcagc ctgggctaca            20

<210> SEQ ID NO 140
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 140
aagcaggaag accatacatt            20

<210> SEQ ID NO 141
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 141
tgctttaatt ccaggatgta            20

<210> SEQ ID NO 142
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 142
tgacaaatgc tttaattcca            20

<210> SEQ ID NO 143
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 143
caaagtgacc taaaccttag            20

<210> SEQ ID NO 144
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 144
tctatataca aagtgaccta            20

<210> SEQ ID NO 145
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 145
caggtttatt ggccataatg            20

<210> SEQ ID NO 146
<211> LENGTH: 20
<212> TYPE: DNA
<213> ORGANISM: Artificial Sequence

```
<220> FEATURE:
<223> OTHER INFORMATION: Oligomeric Compound

<400> SEQUENCE: 146
ccttccctga aggttcctcc                                              20
```

What is claimed is:

1. An antisense oligonucleotide 13 to 80 nucleobases in length consisting of a first region comprising one or more deoxynucleotides and second and third regions flanking said first region, each flanking region comprising at least one 2'-O-(2-methoxyethyl) nucleotide, wherein said oligonucleotide specifically hybridizes within nucleotides 531-693 of SEQ ID NO:1 and inhibits expression of HBXIP.

2. The oligonucleotide of claim 1 which is 13 to 50 nucleobases in length.

3. The oligonucleotide of claim 2 which is 13 to 30 nucleobases in length.

4. The oligonucleotide of claim 3 which is 20 to 30 nucleobases in length.

5. The oligonucleotide of claim 4 which is 20 nucleobases in length.

6. The oligonucleotide of claim 5, wherein said first region comprises 10 nucleobases and said second and third regions each comprise 5 nucleobases.

7. The oligonucleotide of claim 1 further comprising a modified internucleoside linkage at each position.

8. The oligonucleotide of claim 7, wherein the modified internucleoside linkage is a phosphorothioate.

9. The oligonucleotide of claim 1 further comprising at least one modified nucleobase.

10. The oligonucleotide of claim 9, wherein the modified nucleobase is 5-methylcytidine.

11. The oligonucleotide of claim 1 comprising SEQ ID NO: 60.

12. A method of inducing apoptosis of cancer cells, comprising contacting said cells with an oligonucleotide of claim 1 such that apoptosis is induced.

13. The method of claim 12, wherein the cells are derived from the liver.

14. The method of claim 12, wherein the cells are infected with HBV.

15. A method of inhibiting expression of HBXIP in cells or tissues, comprising contacting said cells or tissues with the oligonucleotide of claim 1 such that expression of HBXIP is inhibited.

16. The method of claim 15, wherein the cells or tissues are liver cells or tissues.

17. A method of inhibiting hepatocellular carcinoma tumor growth in an animal, comprising selecting an animal with hepatocellular carcinoma and administering to said animal the oligonucleotide of claim 1.

18. The oligonucleotide of claim 1, comprising any of SEQ ID NOs: 57, 58, 59, 60, 61, 62, 63, 64 and 65.

* * * * *